(12) United States Patent
Kheyfets et al.

(10) Patent No.: US 10,545,122 B2
(45) Date of Patent: Jan. 28, 2020

(54) THERMAL ISOLATION IN A FLUIDIC BLOCK OF AN ACTIVELY CONTROLLING THERMISTOR

(71) Applicant: Waters Technologies Corporation, Milford, MA (US)

(72) Inventors: Greg Kheyfets, Brookline, MA (US); Paul Keenan, Harrisville, RI (US); Joshua A. Shreve, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 215 days.

(21) Appl. No.: 15/555,641

(22) PCT Filed: Feb. 4, 2016

(86) PCT No.: PCT/US2016/016508
§ 371 (c)(1),
(2) Date: Sep. 5, 2017

(87) PCT Pub. No.: WO2016/144447
PCT Pub. Date: Sep. 15, 2016

(65) Prior Publication Data
US 2018/0045691 A1 Feb. 15, 2018

Related U.S. Application Data

(60) Provisional application No. 62/129,547, filed on Mar. 6, 2015.

(51) Int. Cl.
*G01N 30/30* (2006.01)
*G01N 30/02* (2006.01)

(52) U.S. Cl.
CPC ....... *G01N 30/30* (2013.01); *G01N 2030/027* (2013.01); *G01N 2030/3046* (2013.01)

(58) Field of Classification Search
CPC ........... G01N 30/30; G01N 2030/3046; G01N 2030/027
See application file for complete search history.

(56) References Cited

U.S. PATENT DOCUMENTS

| | | | |
|---|---|---|---|
| 3,403,545 A | 10/1968 | Carter | |
| 5,238,557 A * | 8/1993 | Schneider | G01N 30/30 165/164 |

(Continued)

FOREIGN PATENT DOCUMENTS

| | | |
|---|---|---|
| CN | 103376298 A | 10/2013 |
| CN | 203577372 U | 5/2014 |

(Continued)

OTHER PUBLICATIONS

International Preliminary Report on Patentability in International Patent Application No. PCT/US16/16508, dated Sep. 21, 2017; 9 pages.

(Continued)

*Primary Examiner* — Eric S. McCall
*Assistant Examiner* — Timothy P Graves
(74) *Attorney, Agent, or Firm* — Schmeiser, Olsen & Watts LLP

(57) ABSTRACT

A fluidic block has a thermally conductive body with a first end and a second end opposite the first end. The body has a cutout portion formed therein between the first and second ends. The cutout portion partitions the body into a first region, a second region, and a thin region between the first and second regions. The cutout portion produces a thermal break between the first and second regions. The thermal break operates to guide a heat flow between the first and second regions through the thin region. A thermally conductive chromatography tube extends through the first, second, and thin regions from the first end to the second end of the body. The tube is in thermal communication with the (Continued)

body. A section of the tube may run in a transverse direction across the body in the thin region of the body.

25 Claims, 14 Drawing Sheets

(56) References Cited

U.S. PATENT DOCUMENTS

| | | | |
|---|---|---|---|
| 5,983,710 | A | 11/1999 | Uhen et al. |
| 2003/0200795 | A1 | 10/2003 | Gerner et al. |
| 2006/0054558 | A1 | 3/2006 | Jones et al. |
| 2010/0171055 | A1* | 7/2010 | Dourdeville ......... B23K 20/023 251/129.11 |
| 2012/0171773 | A1 | 7/2012 | Murphy et al. |
| 2013/0052083 | A1 | 2/2013 | Kirby et al. |
| 2015/0135861 | A1* | 5/2015 | Cook ..................... G01N 30/30 73/863.12 |

FOREIGN PATENT DOCUMENTS

| | | |
|---|---|---|
| CN | 204065039 U | 12/2014 |
| EP | 0043946 A1 | 1/1982 |
| WO | 2006017820 A1 | 2/2006 |
| WO | 2013133934 A1 | 9/2013 |
| WO | 2014041597 A1 | 3/2014 |

OTHER PUBLICATIONS

International Search Report & Written Opinion in International Patent Application No. PCT/US16/16508, dated Apr. 8, 2016; 11 pages.

U.S. Appl. No. 13/519,818, filed Jan. 11, 2011, by Kirby, et al.; 50 pages.

Extended Search Report in European Patent Application No. 16762092.1 dated Oct. 10, 2018; 8 pages.

* cited by examiner

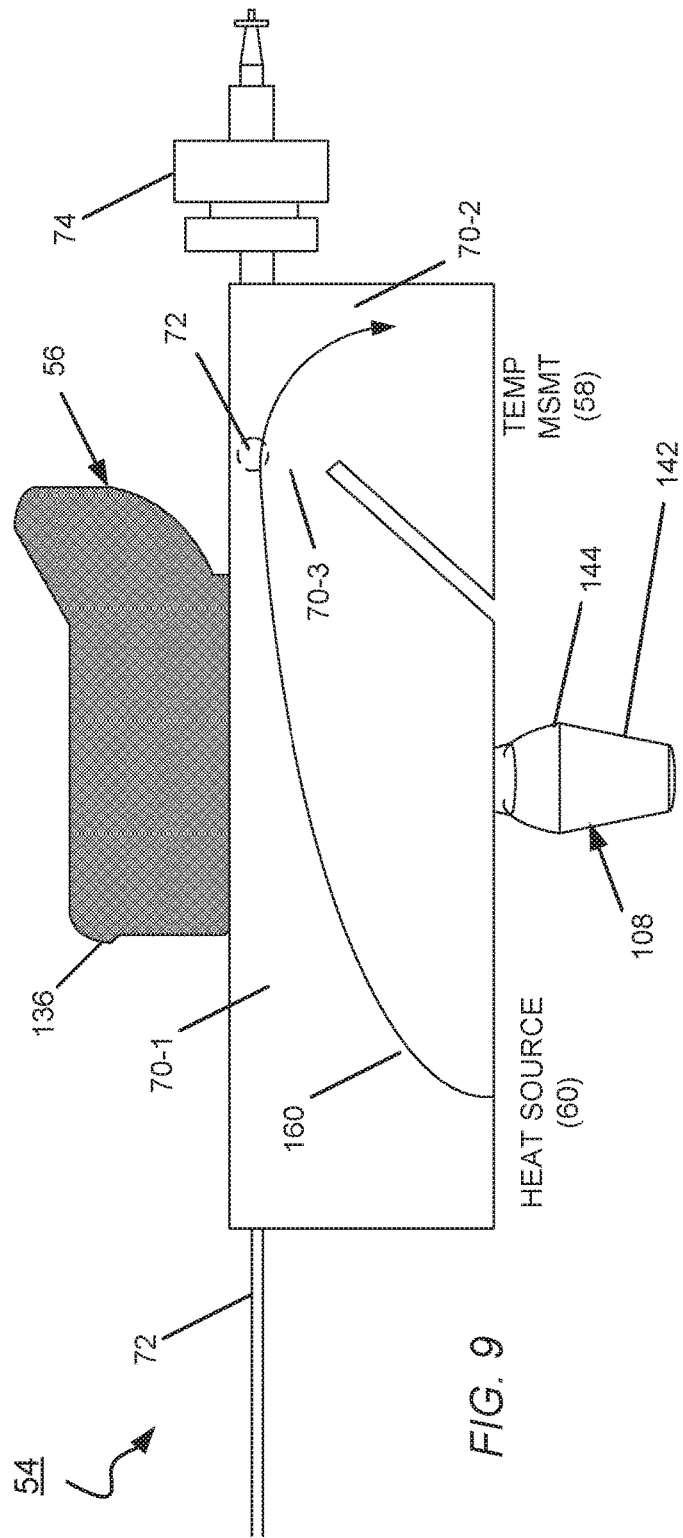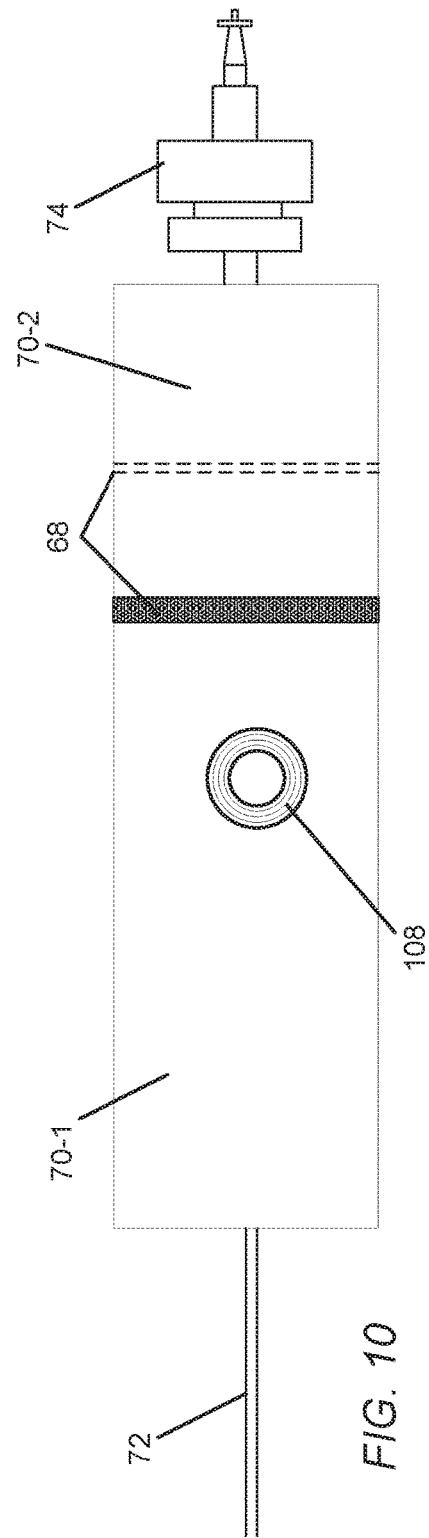
FIG. 9
FIG. 10

THERMAL ISOLATION IN A FLUIDIC BLOCK OF AN ACTIVELY CONTROLLING THERMISTOR

FIELD OF THE INVENTION

The invention relates generally to chromatography systems. More specifically, the invention relates to systems and methods for preheating solvents before entering a column in a chromatographic system.

BACKGROUND

Chromatography is a set of techniques for separating a mixture into its constituents. Generally, in a liquid chromatography analysis, a pump system takes in and delivers a mixture of liquid solvents (and/or other fluids) to a sample manager, where a sample awaits injection into the solvents. The sample is the material under analysis. Examples of samples include complex mixtures of proteins, protein precursors, protein fragments, reaction products, and other compounds, to list but a few. In an isocratic chromatography application, the composition of the liquid solvents remains unchanged, whereas in a gradient chromatography application, the solvent composition varies over time. The mobile phase comprised of a sample dissolved in a mixture of solvents (and/or other fluids), moves to a point of use, such as a separation column, referred to as the stationary phase. By passing the mobile phase through the column, the various components in the sample separate from each other at different rates and thus elute from the column at different times. A detector receives the separated components from the column and produces an output from which the identity and quantity of the analytes may be determined.

Temperature can influence the results of the analysis, affecting such properties as the separation performance of the column and the viscosity of a mobile phase. Therefore, maintaining an accurate constant column temperature is important to the accuracy and reproducibility of the results. The manner by which the column temperature is controlled is an important factor. Convective column-heating systems can produce dispersion because the direct flow of air onto the columns interacts with internal viscous heating to produce radial gradients. An alternative to convective column-heating systems are heated trough designs. However, heated trough designs for long chromatography columns or series of columns can be expensive and a challenge to control.

In addition, accurate preheating of the fluid being delivered to the separation column can be critical to producing consistent retention times. If the temperature of the mobile phase supplied to the column is not constant, for example, for long (e.g., multi-hour) chromatographic runs where the variations in room temperature are significant, the accuracy of the chromatographic analysis can degrade. A device to pre-heat the mobile phase is sometimes used to reduce temperature fluctuations at the column inlet. However, exact control of the mobile phase is difficult to achieve with any system and often involves an offset. Current passive heaters are even less accurate because of lack of feedback.

SUMMARY

All examples and features mentioned below can be combined in any technically possible way.

In one aspect, a fluidic block comprises a thermally conductive body having a first end and a second end opposite the first end. The body has a cutout portion formed therein between the first and second ends. The cutout portion partitions the body into a first region, a second region, and a thin region between the first and second regions. The cutout portion produces a thermal break between the first and second regions. The thermal break operates to guide a heat flow between the first and second regions through the thin region. The fluidic block further comprises a thermally conductive chromatography tube extending through the first, second, and thin regions from the first end to the second end of the body. The tube is in thermal communication with the body.

Embodiments may include one of the following features, or any combination thereof. The tube may be cast or diffusion bonded within the body. A section of the tube may run in a transverse direction across the body in the thin region of the body.

The fluidic block may further comprise a column fitting coupled to one end of the tube. The first region of the fluidic block may be near the first end of the body and the second region may be near the second end of the body, and the cutout portion may angle away from the first end of the body towards the second end of the body. The body of the fluidic block may house no electrical components.

The body of the fluidic block may have a hole extending from a first side of the body through to an opposite, second side of the body; the fluidic block may comprises a retention mechanism including a lever portion movably abutting the first side of the body, a shaft, coupled to the lever portion, extending through the hole in the body; and a plunger coupled to the shaft on the second side of the body, wherein the lever portion has a first position that extends the plunger portion from the hole and a second position that retracts the plunger portion towards the hole. This plunger portion may have a tapered end that widens to a shoulder and from the shoulder narrows to a neck where the plunger meets the shaft, and the body may have circumferential recess in the hole around the shaft; and a spring may be disposed in the recess in the hole around the shaft to provide an opposing force to any force applied to the tapered end of the plunger portion.

Alternatively, the plunger portion may have one or more helical grooves adapted to receive a pin throughout a 90-degree turn of the lever portion. The retention mechanism may further comprise a spring disposed around the shaft, the second side of the body may have one or more exterior-facing ramps formed therein around the hole, and the plunger portion may have one or more prongs facing the one or more ramps, wherein the spring is adapted to urge each prong against one of the one or more ramps throughout a 90-degree turn of the lever portion. In addition, each may have a depressed notch for receiving a tip of one of the one or more prongs when the lever portion is turned into the first position.

In another aspect, a chromatography column pre-heating apparatus comprises a heater assembly having a thermally conductive base and a heater in thermal communication with the base, and a fluidic block coupled to the heater assembly. The fluidic block comprises a thermally conductive body having a first end and a second end opposite the first end. The body has a cutout portion formed therein between the first and second ends. The cutout portion partitions the body into a first region, a second region, and a thin region between the first and second regions. The first region is in thermal communication with the base near the heater of the heater assembly. The cutout portion produces a thermal break between the first and second regions. The thermal break operates to guide conduction of heat produced by the heater from the first region to the second region through the thin region. The fluidic block further comprises a thermally conductive tube extending through the first, second, and thin regions from the first end to the second end of the body. The tube is in thermal communication with the body and heated by the heat produced by the heater.

Embodiments of the column pre-heating apparatus may include one of the following features, or any combination thereof. The tube of the fluidic block may be cast or diffusion bonded within the body of the fluidic block. A section of the tube may run in a transverse direction across the body in the thin region of the body.

The fluidic block may further comprise a column fitting coupled to one end of the tube. The first region may be near the first end of the body and the second region may be near the second end of the body, and the cutout portion may angle away from the first end of the body towards the second end of the body. The body of the fluidic block may house no electrical components.

The body of the fluidic block may have a hole extending from a first side of the body through to an opposite, second side of the body; the fluidic block may comprises a retention mechanism including a lever portion movably abutting the first side of the body, a shaft, coupled to the lever portion, extending through the hole in the body; and a plunger portion coupled to the shaft on the second side of the body, wherein the lever portion has a first position that extends the plunger portion from the hole and a second position that retracts the plunger portion towards the hole. This plunger portion may have a tapered end that widens to a shoulder and from the shoulder narrows to a neck where the plunger meets the shaft, and the body may have circumferential recess in the hole around the shaft; and a spring may be disposed in the recess in the hole around the shaft to provide an opposing force to any force applied to the tapered end of the plunger portion.

Alternatively, the plunger portion may have one or more helical grooves adapted to receive a pin throughout a 90-degree turn of the lever portion. The retention mechanism may further comprise a spring disposed around the shaft, the second side of the body may have one or more exterior-facing ramps formed therein around the hole, and the plunger portion may have one or more prongs facing the one or more ramps, wherein the spring is adapted to urge each prong against one of the one or more ramps throughout a 90-degree turn of the lever portion. In addition, each may have a depressed notch for receiving a tip of one of the one or more prongs when the lever portion is turned into the first position.

In another aspect, a chromatography column module comprises a chromatography column and a pre-heating apparatus coupled to the chromatography column. The pre-heating apparatus comprises a heater assembly having a thermally conductive base and a heater in thermal communication with the base. The pre-heating apparatus further comprises a fluidic block coupled to the heater assembly and to the chromatography column. The fluidic block comprises a thermally conductive body having a first end and a second end opposite the first end. The body has a cutout portion formed therein between the first and second ends. The cutout portion partitions the body into a first region, a second region, and a thin region between the first and second regions. The first region is in thermal communication with the base near the heater of the heater assembly. The cutout portion produces a thermal break between the first and second regions. The thermal break operates to guide conduction of heat produced by the heater from the first region to the second region through the thin region. A thermally conductive tube is coupled to the chromatography column. The tube extends through the first, second, and thin regions from the first end to the second end of the body. The tube is in thermal communication with the body and heated by the heat produced by the heater.

Embodiments of the chromatography column module may include one of the following features, or any combination thereof. A section of the tube may run in a transverse direction across the body in the thin region of the body of the fluidic block. The chromatography column module may further comprise a cover for closing a compartment that houses the chromatography column and the pre-heating apparatus, and wherein the pre-heating apparatus may include a retention mechanism to couple the fluidic block to the heater assembly. This retention mechanism may have a lever portion used to couple the fluidic block to and uncouple the fluidic block from the heater assembly. The lever portion prevents the cover of the compartment from closing when in an uncoupled position, wherein the unclosed cover prevents the heater of the heater assembly from operating.

In still another aspect, a chromatography column pre-heating apparatus comprises a fluidic block comprising a thermally conductive body having a first end and a second end opposite the first end. The body has a cutout portion formed therein between the first and second ends. The cutout portion partitions the body into a first region, a second region, and a thin region between the first and second regions. The first region is in thermal communication with the base near the heater of the heater assembly. The cutout portion produces a thermal break between the first and second regions. The thermal break operates to guide conduction of heat from the first region to the second region through the thin region. A thermally conductive tube extending through the first, second, and thin regions from the first end to the second end of the body. The tube is in thermal communication with the body of the fluidic block.

The chromatography column pre-heating apparatus further comprises a heater assembly coupled to the fluidic block. The heater assembly comprises a thermally conductive base having a cavity and a chamber. The cavity is disposed opposite the first region of the fluidic block and the chamber is disposed opposite the second region of the fluidic block. A heater is disposed within the cavity in thermal communication with the base. The heater producing heat that propagates into the fluidic block. A thermistor assembly is disposed within the chamber of the base. The thermistor assembly has a temperature-sensing element that is substantially isolated thermally from the base. The thermistor assembly has a surface in thermal communication with the second region of the fluidic block to conduct heat from the second region of the fluidic block to the temperature-sensing element. The temperature-sensing element measures temperature of the second region of the fluidic block substantially uninfluenced by a temperature of the base because of the thermal isolation of the temperature-sensing element from the base.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 9 is a side view of the fluidic block of FIG. 5.

FIG. 10 is a bottom view of the fluidic block of FIG. 5.

DETAILED DESCRIPTION

Figure 1:
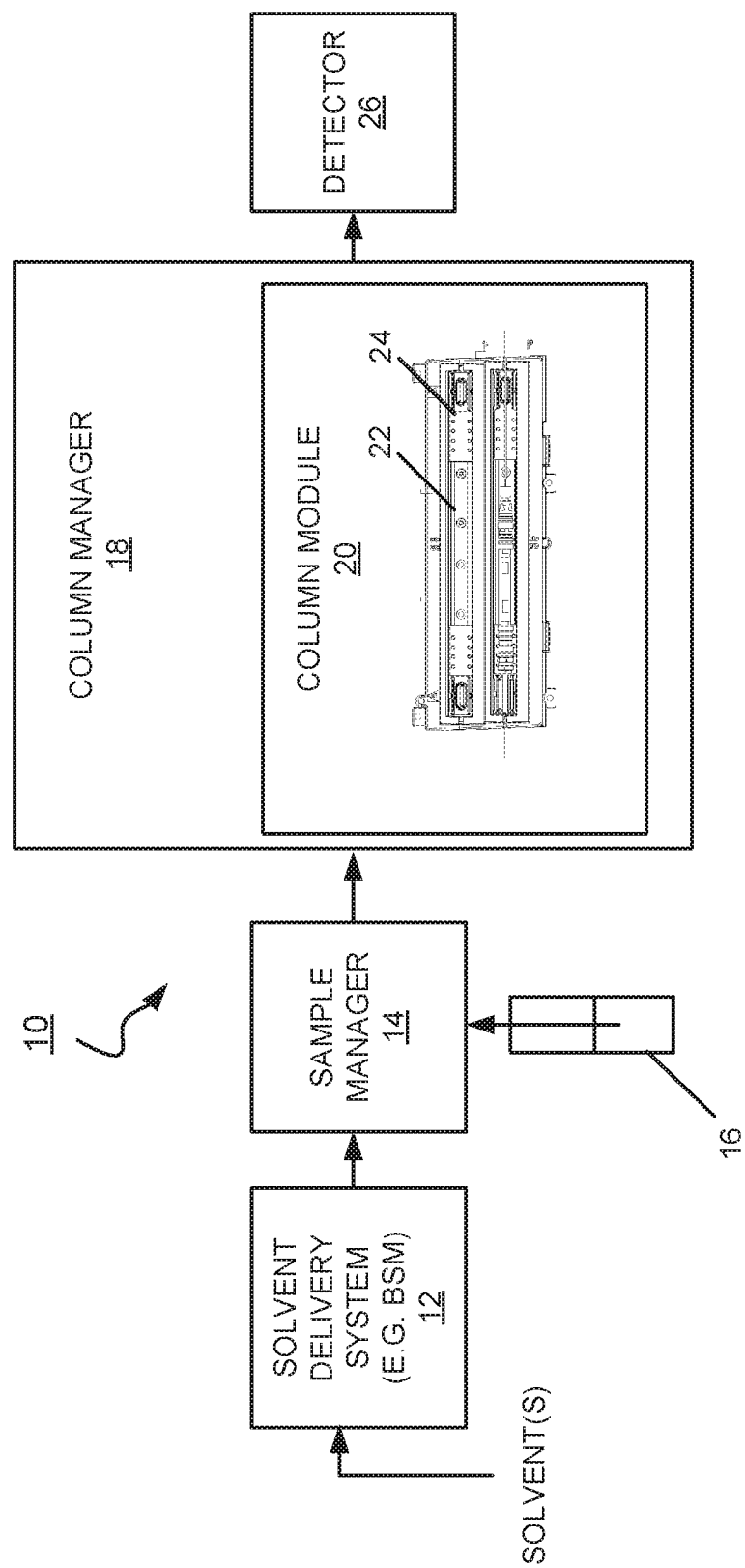
FIG. 1 is a block diagram of an embodiment of a chromatography system.

Embodiments of active pre-heaters described herein include two-piece systems with one piece being a heating (or thermal) base and a second piece being a fluidic block. The fluidic block is a disposable component that houses tubing, which may be cast or bonded into the fluidic block. Making the fluidic block removable advantageously allows for ease of access to connect columns in space-limited locations. The fluidic block has no electrical components, and can, in this sense, be considered passive; the electrical components for controlling the temperature of the fluidic block reside in the thermal base. By embedding all electrical components into a stationary piece built into a column module and having the tubing reside in the separately removable component (i.e., fluidic block), the active pre-heater attains isolation between potential leak source and electrical paths.

The thermal base includes a heater and a controlling temperature-sensing element (or thermistor) assembly. To adjust the temperature of the pre-heater assembly accurately, the measurements made by the thermistor assembly should reflect the temperature of the fluid passing through the tubing. Thermally isolating the thermistor assembly from direct contact with the adjacent heat source in the thermal base enables accurate temperature measurement and any consequent adjustments. The thermistor assembly is spring-loaded to urge thermally conductive contact with the fluidic block in order to read its temperature. In addition, the thermistor assembly is thermally isolated from the thermal base and, thus, reads the temperature with minimal influence from the heated thermal base.

Thermal breaks and engineered heat flow paths in the fluidic block facilitate accurate temperature measurement corresponding to the temperature of the fluid in the tube. A thin cut thermal break in the fluidic block, for example, accompanied by a transverse running section of tubing, forces a heat path through the fluidic path of an active pre-heater before reaching the controlling thermistor assembly. A narrow gap produced by the thermal break, partially blocked by the fluidic tubing across its length, provides a controllable thermal passage. In addition, the side of the thermal base interfacing the electronics is sealed to isolate the electronics from any leakage from the fluidic block. Although designed primarily as an active pre-heater, the apparatus described herein can also operate to cool passively liquid flowing through the fluidic block.

A breakaway attachment mechanism couples the fluidic block to the thermal base. In one embodiment, the attachment mechanism includes a slanted coil spring and a contoured plunger. The shape of the plunger is designed to provide a constant force over a range of tolerances of the fluidic block and thermal base to ensure a consistent gasket compression force. The plunger design does not permit partial insertion into the thermal base and pushes the fluidic block away from the thermal base if not fully installed because of the insertion slope on the plunger. The attachment mechanism produces a tactile snap when the plunger is fully inserted into the spring. The snap connection between the plunger and spring breaks away should a user pull on the column, thereby preventing damage to the active pre-heater. Other embodiments can use different types of springs, for example, a U-shaped spring, a ribbon spring. In addition, the attachment mechanism can alternatively be implemented with a quarter-turn fastener, a bayonet style thumb screw, a threaded thumb screw, or a folded sheet clip. In general, the attachment mechanism can be used for any assembly involving thermal contact, being particularly useful when there are user interface parts, for example, passive pre-heaters, direct column heaters, and sample holders.

FIG. 1 shows an embodiment of a liquid chromatography system 10 for separating a sample into its constituents. The liquid chromatography system 10 includes a solvent delivery system 12 in fluidic communication with a sample manager 14. Generally, the solvent delivery system 12 includes a pump (not shown) in fluidic communication with solvent reservoirs from which the pump draws solvents. The solvent delivery system 12 delivers a mixture of solvents to the sample manager 14. The sample manager 14 is in fluidic communication with a sample source 16 from which the sample manager acquires and introduces a sample to the solvent composition arriving from the solvent delivery system 12. The sample-solvent composition passes to a column manager 18.

The column manager 18 generally provides a controlled temperature environment for one or more chromatography separation columns used in separating sample-solvent compositions. Each separation column is adapted to separate the various components (or analytes) of the sample from each other as the mobile passes through, and to elute the analytes (still carried by the mobile phase) from the column at different times. Embodiments of the separation column include a variety of sizes (e.g., preparative, semi-preparative, analytical, or capillary-scale packed-bed columns or open tubular columns) and a variety of preparations (e.g., in conventional metallic, fused silica, or polymeric tubes, or in metallic, ceramic, silica, glass, or polymeric microfluidic platforms or substrates of various IDs).

The column manager 18 includes a column module 20 that houses one or more thermally conductive troughs 22. Each trough 22 is adapted to hold one or more chromatography columns therein. Either or both ends of each trough 22 have a socket 24 adapted to receive a pre-heater assembly. A pre-heater assembly operates to preheat liquid before the liquid passes to a column disposed within that trough. One example implementation of such a column manager is described in U.S. patent application Ser. No. 13/519,818, filed Jan. 11, 2011, titled, "Column Heater with Active Pre-heating," the entirety of which application is incorporated by reference herein.

From the column manager 18, the constituents of the separated sample pass to a detector 26 or other equipment, for example, a mass spectrometer or a Flame Ionization Detector (FID), for analyzing the separation. The solvent delivery system 12, sample manager 14, column manager 18, and detector 26 may be separate instruments or integrated into a single unit.

Figure 2:
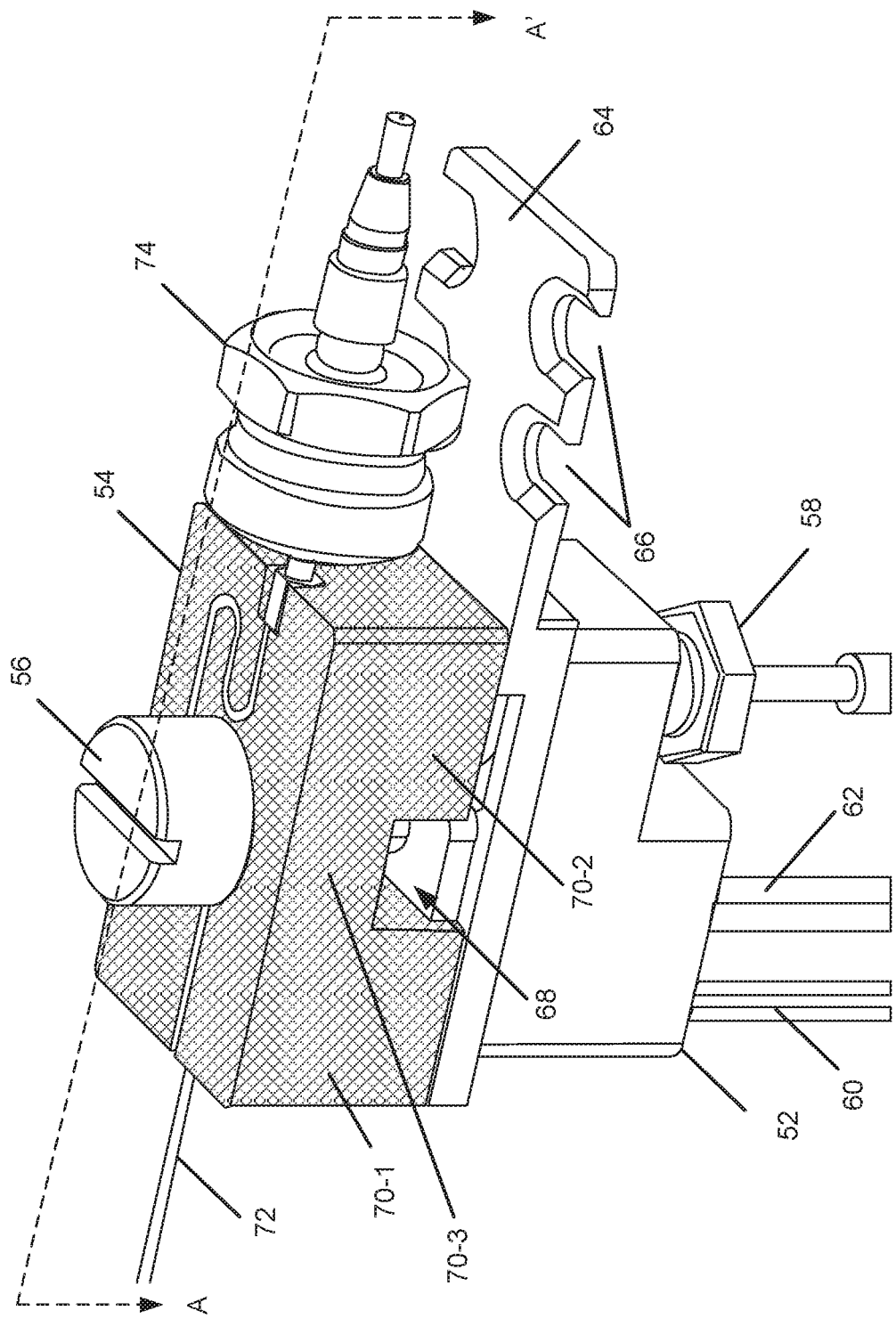
FIG. 2 is an elevated side view of an embodiment of an active pre-heater assembly used to preheat liquid before the liquid enters a chromatography column.

FIG. 2 shows an elevated side view of an embodiment of an active pre-heater assembly 50 that can be used to preheat liquid before the liquid enters a chromatography column. The active pre-heater assembly 50 includes a thermally conductive thermal base 52, a thermally conductive fluidic block 54, and a retention mechanism 56 that holds the thermal base 52 in thermal communication with the fluidic block 54. A thermal gasket (not shown) may be disposed at select regions between the thermal base 52 and the fluidic block 54.

All electronics for controlling the active pre-heater assembly 50 reside in the thermal base 52; the fluidic block 54 has no electrical components and is separately disposable. Advantageously, this absence of electrical components supports a low cost for the fluidic block, particularly making it more readily disposable than if the fluidic block included electronics. This absence also furthers safety by keeping the electronics of the pre-heater assembly 50 away from solvent vapors.

Circuitry (not shown) is in electrical communication with a thermistor assembly 58 (a portion is visible), a heater 60 (only wires are visible), and a safety switch 62 (only wires are visible) embedded within the thermal base 52. As described in more detail below, the thermistor assembly 58 is in thermal communication with the fluidic block 54 and substantially thermally isolated from the thermal base 52. This thermal isolation ensures that the temperature of the fluidic block 54 measured by the thermistor assembly 58 is substantially uninfluenced by the temperature of the thermal base 52. Extending from one side of the thermal base 52 is a mounting plate 64 with holes 66 through which screws can secure the active pre-heater assembly 50 to a corresponding holes in a column trough 22 (FIG. 1).

The fluidic block 54 is generally rectangular in shape and may have a cutout section 68 formed therein that forms a thermal break between regions 70-1, 70-2 of the fluidic block 54. The thermal break operates to guide and concentrate the flow of heat from one region 70-1 to the other region 70-2 through a thin region 70-3 of the fluidic block 54 formed by the cutout section 68. This thin region 70-3 resides "above" the cutout section 68 between the first and second regions 70-1, 70-2. It is to be understood that such terms like above, below, upper, lower, left, right, top, bottom, front, and rear are relative terms used for purposes of simplifying the description of features as shown in the figures, and are not used to impose any limitation on the structure or use of the active pre-heater assembly 50. In addition, although described in terms of discrete first, second, and thin regions 70-1, 70-2, and 70-3, respectively, the fluidic block 54 is an integral unit; the dividing of the fluidic block 54 into regions is for facilitating the description. Some embodiments of the active pre-heater assembly 50 may lack a cutout section 68, and, hence, have no corresponding thin region 70-3. Tubing 72 extends through the first, second, and thin regions 70-1, 70-2, 70-3, respectively, of the fluidic block 54, taking a serpentine path, and coupling to a column fitting 74 for making a fluidic connection with a chromatography column. The tubing 72 may be cast or diffusion bonded into the fluidic block 54. The fluidic block 54, with the tubing 72 and column fitting 74, can be an integral unit (i.e., distributed or sold as a single component).

The heater 60 and safety switch 62 within the thermal base 52 are disposed directly opposite the first region 70-1 of the fluidic block 54, where the liquid in the tubing 72 first enters the fluidic block 54. The thermistor assembly 58 within the thermal base 52 is disposed directly opposite the second region 70-2 of the fluidic block 54, where the liquid in the tubing 72 leaves the fluidic block 54.

The retention mechanism 56 includes a screw that enters an appropriately sized opening (obscured by the head of the screw) in a top side of the fluidic block 54, passes entirely through the fluidic block 54, and fastens into an appropriately sized opening in a top side of the thermal base 52.

In brief overview, liquid from the sample manager 14 (FIG. 1) flows through the tubing 72 to the column fitting 74. The other end of the tubing 72, opposite the column fitting 74, can also have a fitting for coupling to the sample manager 14. Circuitry actively controls the temperature of the thermal base 52 by controlling operation of the heater 60. The safety switch 62 measures the temperature of the thermal base 52 near the heater 60 and may operate to disable the heater 60 should its measured temperature exceed a threshold. The thermally conductive thermal base 52 conducts the heat generated by the heater 60 to the fluidic block 54, predominantly through the first region 70-1. Heat flows from the first region 70-1 of the fluidic block to the second region 70-2 of the fluidic block across the thin region 70-3 (if there is a cutout region 68 forming a thermal break). In general, substantially no heat flows directly from the thermal base 52 to the second region 70-2 of the fluidic block 54; other than with the thermistor assembly 58, which is thermally isolated from the thermal base 52, the second region 70-2 of the fluidic block 54 makes substantially no thermally conductive contact with the thermal base 52. The thermistor assembly 58 measures the temperature of the second region 70-2 of the fluidic block 54, where the liquid in the tubing 72 enters the column fitting 74. This measured temperature closely or exactly corresponds to the temperature of the liquid in the tubing 72 as the liquid enters the column fitting 74.

Figure 3:
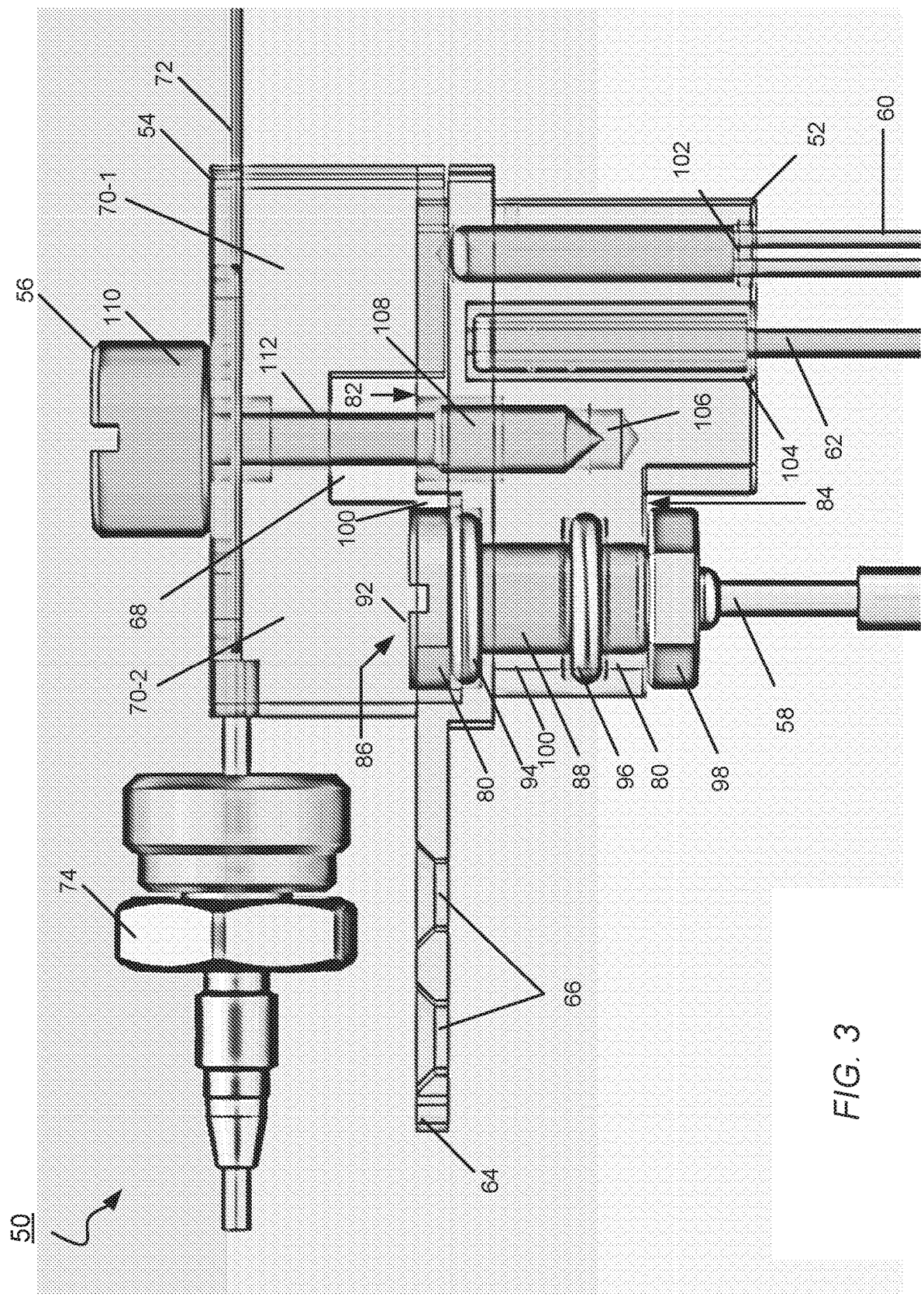
FIG. 3 is a transparent side view of the embodiment of the active pre-heater assembly 50 of FIG. 2, including a thermal base and a fluidic block.

FIG. 3 shows a transparent side view of the embodiment of the active pre-heater assembly 50 of FIG. 2, including the thermally conductive thermal base 52, thermally conductive fluidic block 54, and retention mechanism 56. The thermal base 52 has a chamber 80 for receiving the thermistor assembly 58. The chamber 80 extends through a thickness of the thermal base 52, from a top side 82 that interfaces the fluidic block 54 through to a bottom side 84 through which the wires of the various electrical components extend.

One embodiment of the thermistor assembly 58 includes a body comprised of a spring-loaded screw 86 having a neck region 88 below a slotted head region 90. The head region 90 has a generally planar surface 92 (with, for example, a screwdriver slot) that extends above the plane of the top side 82 of the thermal base 52. A temperature-sensing element (or thermistor) is housed within and in thermal communication with the neck and head regions 88, 90, respectively, of the screw 86. An air gap 100 surrounds the head region 90 and most of the neck region 88 to facilitate thermally isolating these regions from the thermal base 52.

A spring 94 is disposed around the neck region 88 under the head region 90 of the screw 86. The action of the spring 94 resists any force applied to the head region 90 that urges the screw 86 into the chamber 80, such as occurs when joining the fluidic block 54 to the thermal base 52. The spring 94 counters such force by urging the generally planar surface 92 against the underside of the fluidic block 54. Embodiments of the spring 94 include, but are not limited to, a canted-coil spring, a coil spring, and an o-ring. The screw 86 "floats" within the chamber 80 on this spring 94.

An O-ring 96 can be disposed around the lower portion of the neck region 88 of the screw 86 to block any leakage from propagating through the bottom side 84 towards the electronics of the thermistor assembly 58. Alternatively, drainage features can be used instead of a seal. A nut 98 secures the thermistor assembly 58 to the thermal base 52 from the bottom side 84.

The thermal base 52 also has a first cavity 102 for receiving the heater 60, a second cavity 104 for receiving the safety switch 62, and a third cavity 106 for receiving a plunger portion 108 of the retention mechanism 56. The first and second cavities 102, 104 open on the bottom side 84, and do not have an opening on the top side 82 (thereby, not providing a leakage path), whereas the third cavity 106 has an opening on the top side 82. The retention mechanism 56 also includes a slotted head portion 110 and a shaft 112 with the plunger portion 108 at its end. In this example, the shaft 112 extends through the thin region 70-3 of the fluidic block 54. Threads of the plunger portion 108 tighten within the third cavity 106 and anchor the fluidic block 54 to the thermal base 52. With the thermal base 52 in thermal communication with the fluidic block 54, as shown, the heater 60 in the first cavity 102 almost abuts the underside of the first region 70-1 of the fluidic block 54 and the exposed planar surface 92 of the head region 90 of the thermistor assembly 58 abuts the underside of the second region 70-2 of the fluidic block 54.

Figure 4:
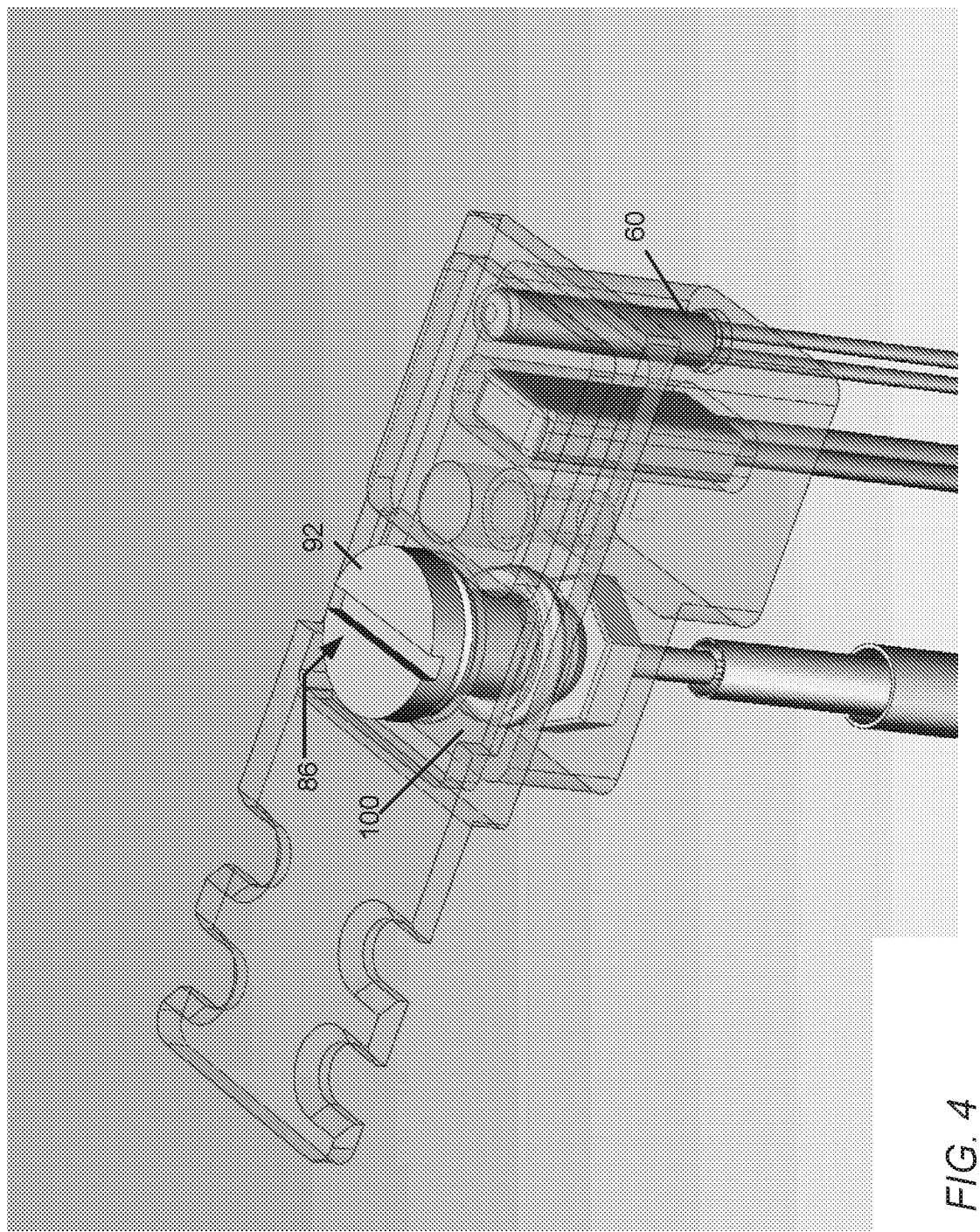
FIG. 4 is an elevated view of the embodiment of the thermal base.

FIG. 4 shows an elevated view of the embodiment of the thermal base 52 to illustrate further the air gap 100 surrounding the head region 90 of the spring-loaded screw 86 in order to provide thermal isolation of the thermistor assembly 58 from the thermal base 52. The air gap 100 operates to insulate the head region 90 from the heat conducted by the thermal base 52 from the heater 60.

Figure 5:
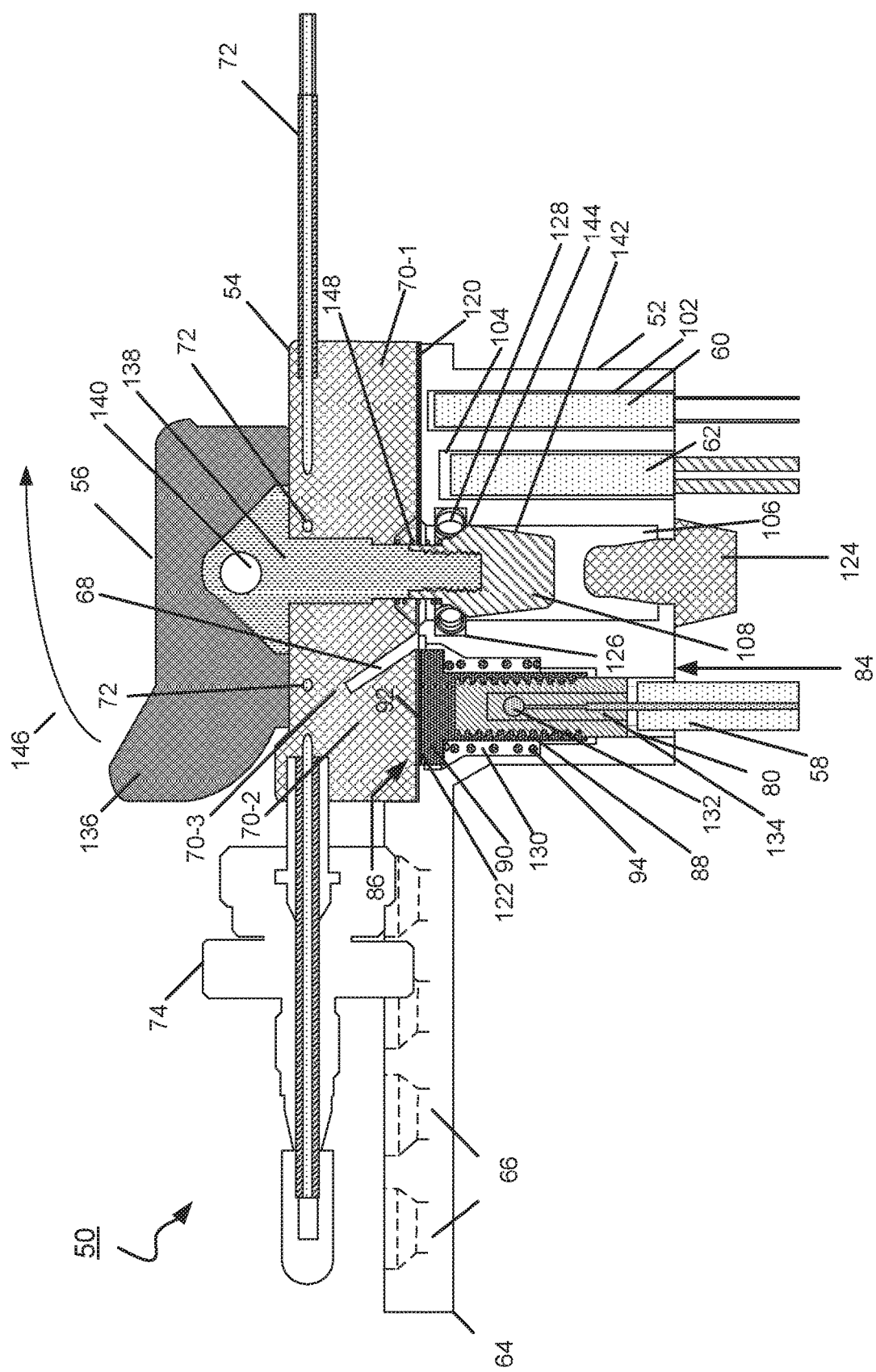
FIG. 5 is a cross-sectional side view of another embodiment of an active pre-heater assembly including a thermal base and fluidic block.

FIG. 5 shows a cross-sectional side view of another embodiment of an active pre-heater assembly 50. The cross-sectional side view is along a line similar to and reverse of the line A-A' in FIG. 2. This embodiment of active pre-heater assembly 50 includes a thermally conductive thermal base 52, a thermally conductive fluidic block 54, and a retention mechanism 56 that holds the thermal base 52 in thermal communication with the fluidic block 54. A thermal gasket 120 is disposed between the region 70-1 of the thermal base 52 and the fluidic block 54. Another thermal gasket 122 is disposed between the region 70-2 of the thermal base 52 and the head region 90 of the thermistor assembly 58. This gasket 122 is sized appropriately to match the dimensions of the planar surface 92 of the head region 90, thereby thermally coupling the region 70-2 of the thermal base 52 with the head region 90, but with substantially no other portion of the thermal base 52.

Similar to the example of FIG. 2, all electronics for controlling the active pre-heater assembly 50 of FIG. 5 reside in the thermal base 52, and the fluidic block 54 has no electrical components and is separately disposable. The thermal base 52 has a chamber 80 for receiving the thermistor assembly 58, a first cavity 102 for receiving the heater 60, a second cavity 104 for receiving the safety switch 62, and a third cavity 106 for receiving the plunger portion 108 of the retention mechanism 56. A plug 124 seals the end of the third cavity 106 at the bottom side 84 of the thermal base 52. The third cavity 106 also includes a circumferential pocket 126 within which is disposed a slanted-coil spring 128. (Other embodiments include, but are not limited to, a ribbon spring). A mounting plate 64 with holes 66 extend from one side of the thermal base 52. Fasteners inserted through these holes 66 can secure the active pre-heater assembly 50 to a corresponding holes in a column trough 22 (FIG. 1).

This example of the fluidic block 54 is generally rectangular in shape (about 1 to 2 inches in length, and less than 1 inch in width) and has a cutout section 68 formed diagonally in the fluidic block 54. The cutout region 68 is a thin slice or cleft at approximately a minus 45 degree angle with respect to a bottom side of the fluidic block 54 (the cleft angles upwards towards the liquid-egress end of the fluidic block 54). The air gap produced by the cleft forms a thermal break between regions 70-1, 70-2 of the fluidic block 54. In addition, the thinness of the cleft does not consume much area of the fluidic block used to heat the liquid passing through the tubing 72. The thermal break operates to guide and concentrate the flow of heat from one region 70-1 to the other region 70-2 through a thin region 70-3 of the fluidic block 54 formed by the cutout section 68. This thin region 70-3 resides "above" the cutout section 68 between the first and second regions 70-1, 70-2. Again, some embodiments of the active pre-heater assembly 50 may lack a cutout section 68, and, hence, have no corresponding thin region 70-3.

Tubing 72 extends through the first, second, and thin regions 70-1, 70-2, 70-3, respectively, of the fluidic block 54, taking a serpentine path, and coupling to a column fitting 74. Some lengths of the tubing 72 run perpendicular to the plane shown in FIG. 5 and appear as circles 72 in the cross-sectional drawing. One of the circles corresponding to the tubing 72 appears in the thin region 70-3 of the fluidic block 54, to enhance heating of the liquid in the tubing 72, as described in more detail in connection with FIG. 9. The tubing 72 may be cast or diffusion bonded into the fluidic block 54, and the fluidic block 54, with the tubing 72 and column fitting 74, can be an integral unit (i.e., distributed or sold as a single component).

The heater 60 and safety switch 62 disposed within the thermal base 52 are directly opposite the first region 70-1 of the fluidic block 54, where the liquid in the tubing 72 first enters the fluidic block 54. The thermistor assembly 58 within the thermal base 52 is disposed directly opposite the second region 70-2 of the fluidic block 54, where the liquid in the tubing 72 leaves the fluidic block 54.

This example of the thermistor assembly 58 includes a spring-loaded screw (or fitting) 86 having a neck region 88 below a head region 90. The head region 90 has a generally planar surface 92. A spring 94 is disposed in a pocket 130 around the neck region 88 under the head region 90 to resist any force applied to the head region 90 that urges the screw 86 into the chamber 80, such as occurs when joining the fluidic block 54 to the thermal base 52. The spring 94 operates to urge the generally planar surface 92 against the underside of the fluidic block 54. The inner diameter of the chamber 80, contoured to follow the shape of the neck and head regions 88, 90, is slightly larger than the outer diameters of the head region 90 and neck region 88, to provide a surrounding air gap that facilitates thermally isolating these regions from the thermal base 52. The screw 86 "floats" within the chamber 80 on this spring 94, substantially isolated thermally from the thermal base 52.

A temperature sensing component 132 is housed within a hollow 134 of the neck region 88. In response to the application and removal of force applied on the spring 94, the spring-loaded screw moves down or up within the pocket 130 in the chamber 80; conversely, the temperature sensing component 132 moves correspondingly up or down within the hollow 134 of the neck region 88. With the screw 86 fully depressed within the chamber 80, the temperature sensing component 132 can make physical contact with the interior ceiling and sides of the hollow 134 to place the temperature sensing component 132 in thermally conductive contact with the neck region 88; accordingly, heat conducted through the head region 90 reaches the thermal sensing component 132. The thermal isolation provided by the air gap surrounding the head region 90 ensures that the temperature measured by the temperature sensing component 132 is predominantly determined by the temperature of the fluidic block 54, specifically, of the region 70-2 where the liquid passing through the tubing 72 leaves the fluidic block 54 and enters the column fitting 74.

Other techniques may be employed to thermally isolate the thermistor assembly 58 from the thermal base 52. Instead of floating on a spring, the screw 86 can be wrapped in a plastic insulator, mounted on thermally isolated components, or spatially separated from the chamber walls with rubber o-rings and plastic components. Advantageously, use of the spring 94 ensures physical contact of the underside of the fluidic block 54 by the planar surface 92 of the screw 86; the spring 94 compensates for tolerances in the manufacture of the thermal base 52 and fluidic block 54.

This example of retention mechanism 56 includes a finger-manipulated lever 136 coupled to a contoured plunger portion 108 by a shaft 138. The plunger portion 108 has a tapered end 142 that widens up to a shoulder 144 and then narrows to a neck above the shoulder 144. This shape of the plunger is designed to provide a constant force over a range of tolerances of the fluidic block 54 and thermal base 52 to ensure a consistent gasket compression force. In one embodiment, the plunger portion 108 is constructed of a resilient material, like some plastics. A spring 148 is disposed around the shaft 138 and around the neck of the plunger portion 108.

The finger-manipulated lever 136 is rotatable about an axis defined by a pin 140 that couples the lever 136 to the shaft 138. A user pushes on the lever 136 to couple the fluidic block 54 to the thermal base 52. When the fluidic block 54 is joined to the thermal base 52, the finger-manipulated lever 136 lays flush on the surface of the fluidic block 54, as shown. Rotating the lever 136 about the pin 140 in the direction indicated by the arrow 146 operates to provide enough leverage to pull the plunger portion 108 out of the spring 128, thereby separating the fluidic block 54 from the thermal base 52.

When the retention mechanism 56 operates to join the fluidic block 54 to the thermal base 52, the plunger portion 108 penetrates the third cavity 106 of the thermal base 52. The tapered end 142 of the plunger portion 108 passes through the ring formed by the spring 128. The width of the plunger portion 108 at the shoulder 144 is wider than the ring formed by the spring 128; accordingly, the plunger portion 108 meets resistance when the shoulder 144 comes into contact with the spring 128. With additional force on the lever 136, the shoulder 144 deforms the spring 128 sufficiently to push through the ring. When the plunger portion 108 penetrates the ring beyond its shoulder 144, the plunger portion 108 pulls itself into the spring 128, producing a tactile "snap", with the spring 128 springing back to its normal shape around the shoulder 144 of the plunger portion 108. The snap assures the user that the fluidic block 54 is properly joined to the thermal base 52. In addition, the shape of the plunger portion 108 does not permit partial insertion into the spring 128; the insertion slope on the plunger portion 108 pushes the fluidic block 54 away from the thermal base 52 if the shoulder 144 of the plunger portion 108 is not fully installed within the spring 128.

The snap connection between the plunger portion 108 and the spring 128 will also break away non-destructively should a user pull on the column. The fluidic block 54 decouples from the thermal base 52 when the force pulling the plunger portion 108 and spring 128 apart exceeds the force of the spring 128 holding the plunger portion 108 in place. This breakaway attachment mechanism prevents damage to the active pre-heater assembly 50.

Other embodiments of retention mechanisms 56 that may be used include, but are not limited to, thumbscrews and bayonet grip screws. Some embodiments can permanently attach the fluidic block 54 to the thermal base 52, in which instances, the fluidic block 54 is not separately disposable.

Figure 6:
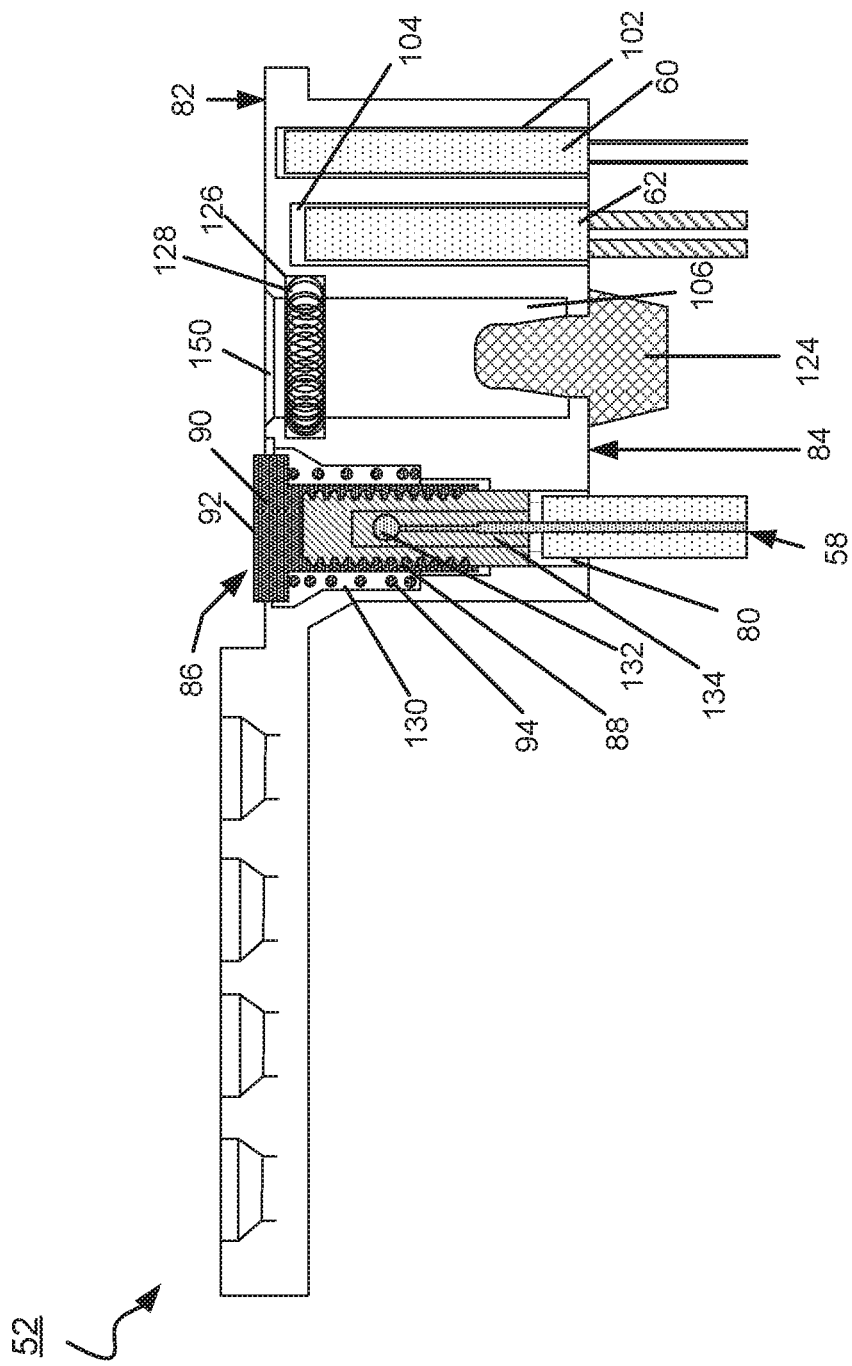
FIG. 6 is a cross-sectional side view of the thermal base of FIG. 5, separated from the fluidic block.

FIG. 6 shows the cross-sectional side view of the thermal base 52 of FIG. 5, separated from the fluidic block 54. When the thermal base 52 is not joined to the fluidic block 54, the spring 94 around the neck region 88 of the thermistor assembly 58 urges the head region 90 of the spring-loaded screw 86 out of the chamber 80. As a result, the planar surface 92 of the head region 90 is above the plane of the top side 82 of the thermal base 52. This same force of the spring 94 urges the planar surface 92 against the bottom of the fluidic base 54 when the two pieces (52, 54) are joined.

Also shown is a top-side opening 150 into the third cavity 106 of the thermal base 52 into which the plunger portion 108 enters when the thermal base 52 and fluidic block 54 are joined. This view also illustrates the position of the slanted-coil spring 128 within the pocket 126 in the third cavity 106 near its opening 150.

Figure 7:
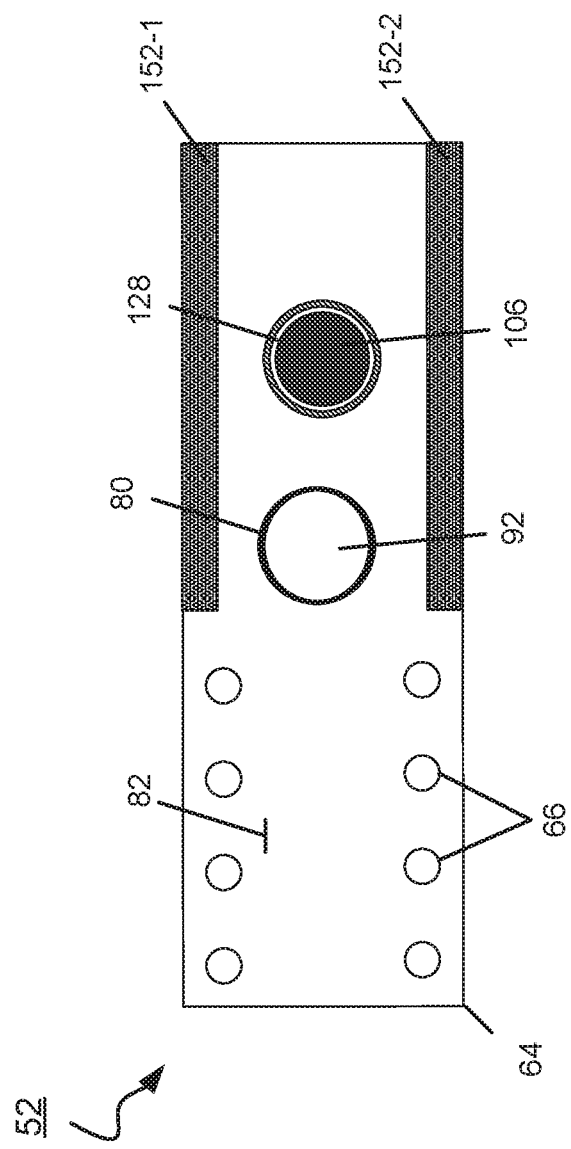
FIG. 7 is a plan view of the thermal base of FIG. 5.
Figure 8:
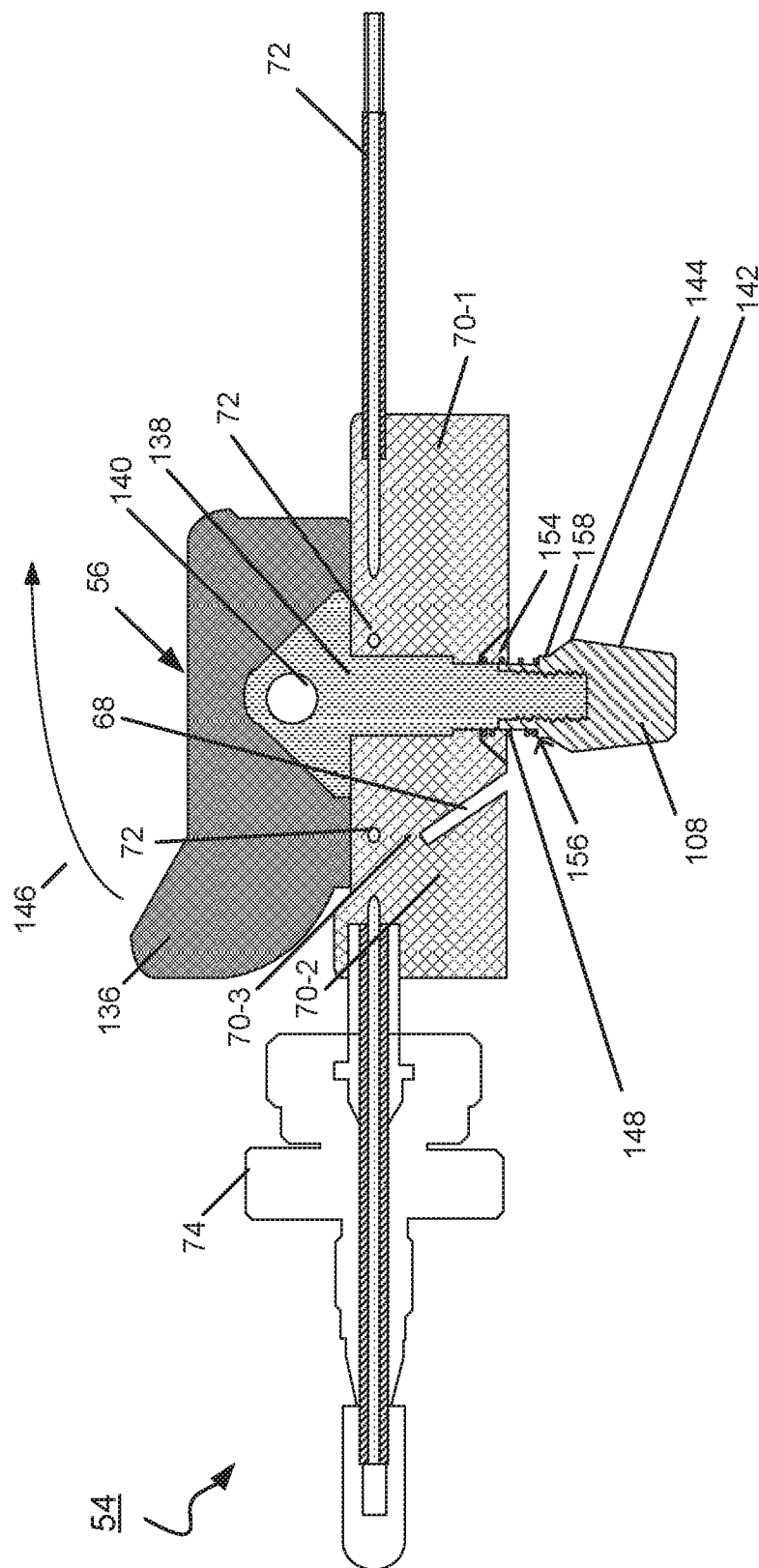
FIG. 8 is a cross-sectional side view of the fluidic block of FIG. 5.

FIG. 7 shows a plan view of the thermal base 52 of FIG. 5, showing the mounting plate 64 with holes 66, the planar surface 92 of the spring-loaded screw 86 within the chamber 80, and the opening 150 into the third cavity 106 that has the pocket 126 with the slanted-coil spring 128. Rectangular depressions 152-1, 152-2 serve as rails used to align and receive corresponding edges of the fluidic block 54 (for when the base 52 and block 54 are joined), FIG. 8 shows the cross-sectional side view of the fluidic block 54 of FIG. 5, separated from the thermal base 52. This view more clearly shows the spring 148 disposed around the shaft 138 of the retention mechanism 56. The spring 148 is lodged between a recess 154 within the fluidic block 54 and a rim 156 around the neck 158 of the plunger portion 108. The spring 148 "stiffens" the plunger portion 108 when the plunger portion 108 enters the third cavity of the thermal base 52 and presses against the slanted-coil spring 128.

FIG. 9 shows a side view of the fluidic block 54 of FIG. 5 (from the opposite side of that shown in FIG. 8), including the lever 136 and plunger portion 108 of the retention mechanism 56. This view shows a general direction (arrow 160) of heat flow of heat through the fluidic block 54 caused by the thermal break (i.e., cutout region 68). The heat generally flows from the first region 70-1, which is heated by the heat source (i.e., the heater 60; FIG. 5), around the thermal break 68, to the second region 70-2, passing through the thin region 70-3. The thermal break 68 operates to guide and concentrate the flow of heat through this thin region 70-3. Within this thin region 70-3, the tubing 72 runs generally parallel to the horizontal direction of the thermal break 68 (i.e., perpendicular to the plane of FIG. 9), thereby maximizing an amount of tubing exposed to the concentrated flow of heat passing through the region and consequent heating of liquid within the tubing. The measurement of temperature (performed by thermistor assembly 58; FIG. 5) occurs at the region 70-2 where the liquid leaves the fluidic block 54 and enters the column fitting 74.

FIG. 10 shows a bottom view of the fluidic block 54 of FIG. 5, including the bottom of the plunger portion 108 and opening into the cutout region 68 that produces a thermal break between regions 70-1 and 70-2 (the dashed lines show where the cutout region 68 ends within the fluidic block 54).

Figure 11:
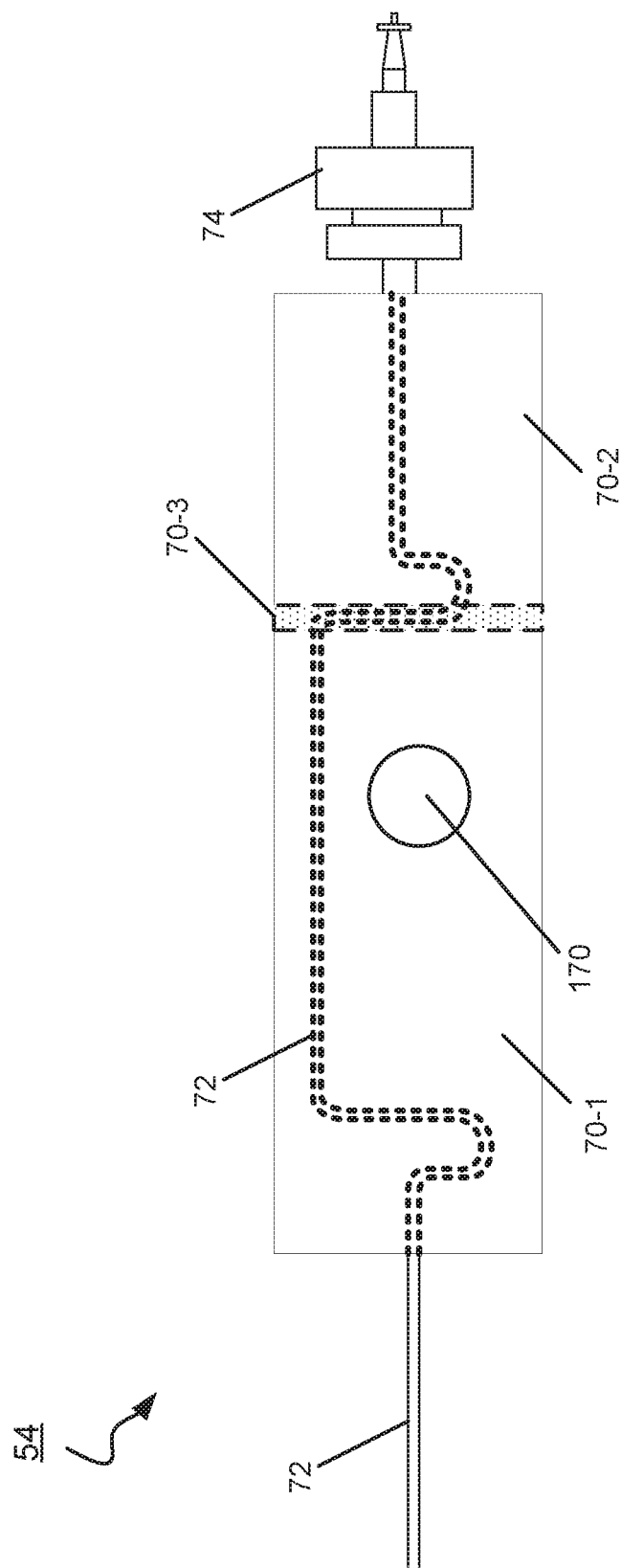
FIG. 11 is a plan view of the fluidic block of FIG. 5.

FIG. 11 shows a plan view of the fluidic block 54 of FIG. 5 with serpentine tubing 72 passing therethrough. The retention mechanism 56 (FIG. 5) is absent from the drawing to show an opening 170 into the fluidic block 54 through which the shaft 138 (FIG. 5) passes. The serpentine tubing 72 circumvents the opening 170 and runs above the thermal break 68 in the thin region 70-3 of the fluidic block. Other serpentine paths can be devised to ensure the liquid heats to the desired temperature.

Figure 12:
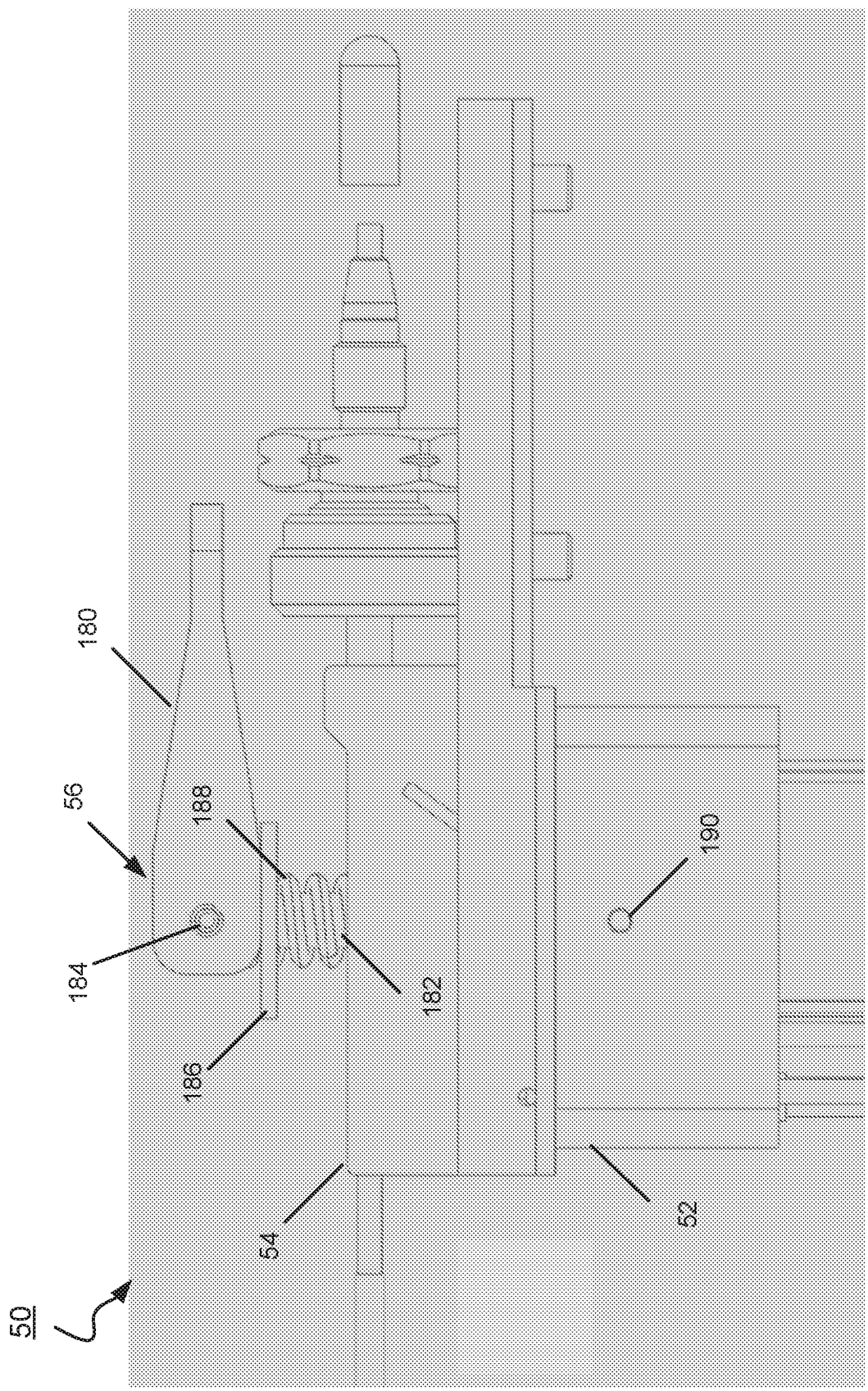
FIG. 12 is a side view of an embodiment of an active pre-heater assembly with another embodiment of a retention mechanism for joining the fluidic block to the thermal base.

FIG. 12 shows a side view of an active pre-heater assembly 50 with another embodiment of a retention mechanism 56 for joining the fluidic block 54 to the thermal base 52. The retention mechanism 56 includes a lever 180 coupled to a shaft 182 by a pin 184. The pin 184 coincides with an axis of rotation (perpendicular to the page of the figure). The lever 180 abuts a washer 186, which serves as a fulcrum. A spring 188 is disposed around the shaft 182 below the washer 186.

In FIG. 12, the retention mechanism 56 is in locked position, securing the fluidic block 54 to the thermal base 52, as described in more detail in connection with FIG. 13. A pin 190 passes entirely through the thermal base 52 (the ends of the pin 190 may be flush with the outer surfaces of the sides of the thermal base 52). When the retention mechanism 56 is in the locked position, one end of the shaft 188 (obscured by the thermal base 52) hooks this pin 190.

Figure 13:
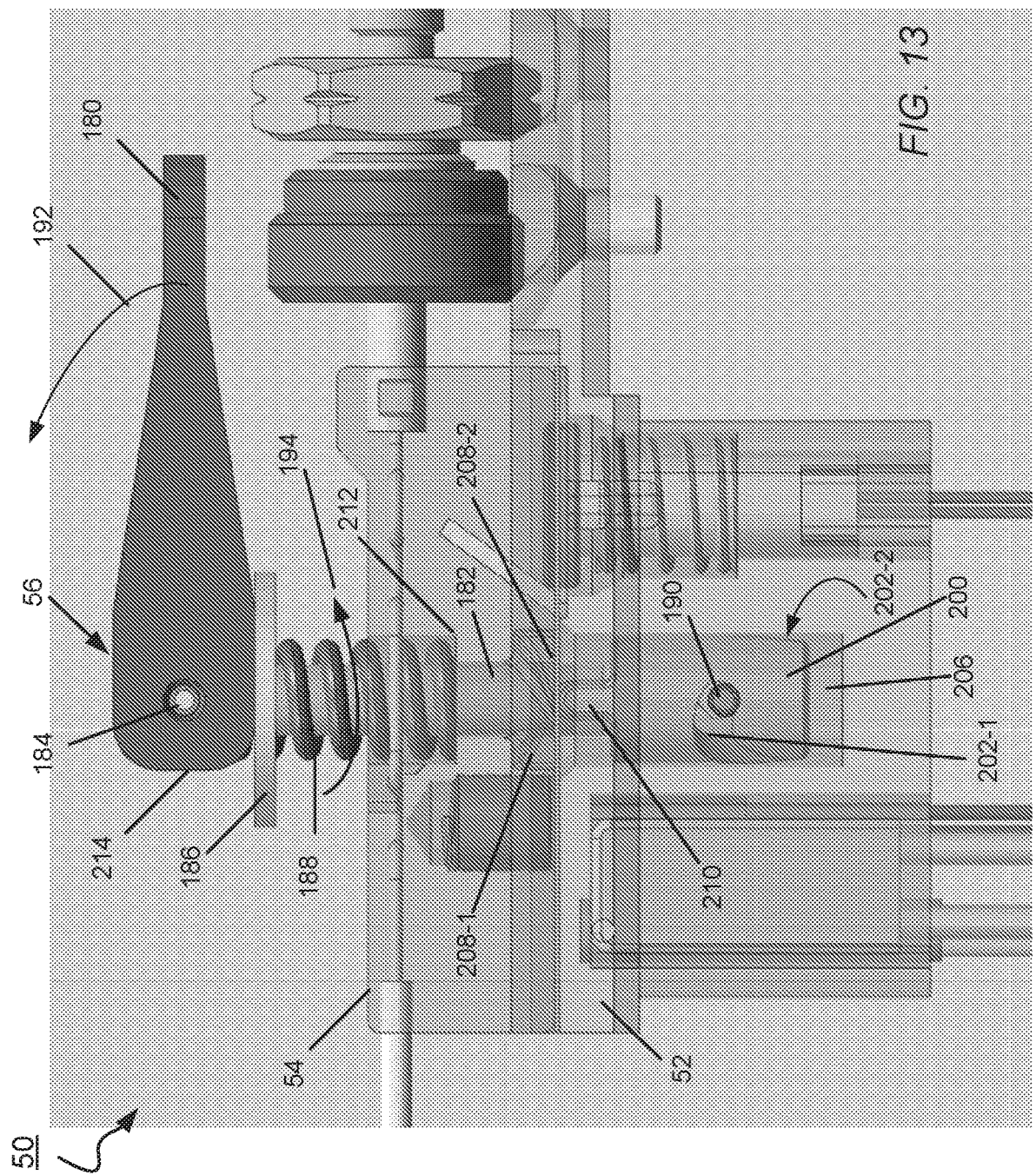
FIG. 13 is a transparent side view of the active pre-heater assembly of FIG. 12, showing the retention mechanism extending through the fluidic block into the thermal base.

FIG. 13 shows a transparent side view of the active pre-heater assembly 50 of FIG. 12, with the retention mechanism 56 extending through the fluidic block into the thermal base. The shaft 182 of the retention mechanism 56 widens to a plunger portion 200. The plunger portion 200 has a pair of helical grooves 202-1, 202-2 (generally, 202) that are rotationally symmetric on opposite sides of the plunger portion 200. In FIG. 13, the grooves 202 align at the closed end of each helical groove 202, where the pin 190 of the thermal base 52 rests when the retention mechanism 56 is locked. The pin 190 extends across a diameter of a cavity 206 formed in the thermal base 52 for closely receiving the plunger portion 200.

Formed in the bottom of fluidic block 52 are a pair of arcuate ramps 208-1, 208-2 (generally, 208). Each ramp 208 receives a round tipped prong 210 formed on the side of the plunger portion 200. The prongs 210 are on opposite sides of the plunger portion 200. Each prong 210 moves within its respective ramp 208 when the retention mechanism 56 turns.

In FIG. 13, the retention mechanism is in the locked position, wherein the spring 188 is compressed between the washer 186 and a cavity floor 212 within the fluidic block 52. With the spring 188 so compressed, each prong 210 is urged into a depression (FIG. 15) in a respective ramp 208, which holds the plunger portion 200 in place. In addition, because of the force produced by the spring 188, which urges the plunger portion 200 out of the cavity 206, the ends of the helical grooves 202 pull up on the pin 190 of the thermal base 52. This force thus urges the thermal base 52 against the fluidic block 54 for improved thermal contact.

Unless the retention mechanism 56 is in the locked position, the front cover of the column module 20 (FIG. 1) will not close; and when the front cover does not fully close, the pre-heater assemblies 50 will not operate. This safety mechanism ensures that the fluidic block 54 is correctly joined to the thermal base 52 before heating can occur.

To unlock the retention mechanism 56, an individual can lift the lever 180 in a direction illustrated by arrow 192, rotating the lever 180 about the pin 184. The lifting of the lever 180 operates to move the plunger portion 200 deeper into the cavity 206, moving the edge of the helical grooves 202 away from the pin 190. A flat surface of the lever 180 permits the individual to lift the lever 180 into a vertical position, at which position the lever 180 may be freely turned.

With the lever 180 in the vertical position, the individual then turns the lever 180 by 90 degrees (in this embodiment, counterclockwise, as illustrated by arrow 194). This quarter-turn operates to rotate the plunger portion 200, moving each prong 210 within its respective ramp 208 out of the depression, within which the prong 210 previously sat, into a lower region of the ramp 208. In addition, the rotation of the plunger portion 200 changes the location of the pin 190 within each helical groove 202; the pin 190 moves towards the open end of each helical groove 202. The movement of the pin 190 within the grooves 202 and the prongs 210 within the ramp 208 cooperate with the force of the compressed spring 188 that urges the plunger portion 200 out of the cavity 206. After the pin 190 exits the grooves 202, the plunger portion 200 is no longer secured to the thermal base 52, and the thermal base 52 can be pulled apart from the fluidic block 54.

Figure 14:
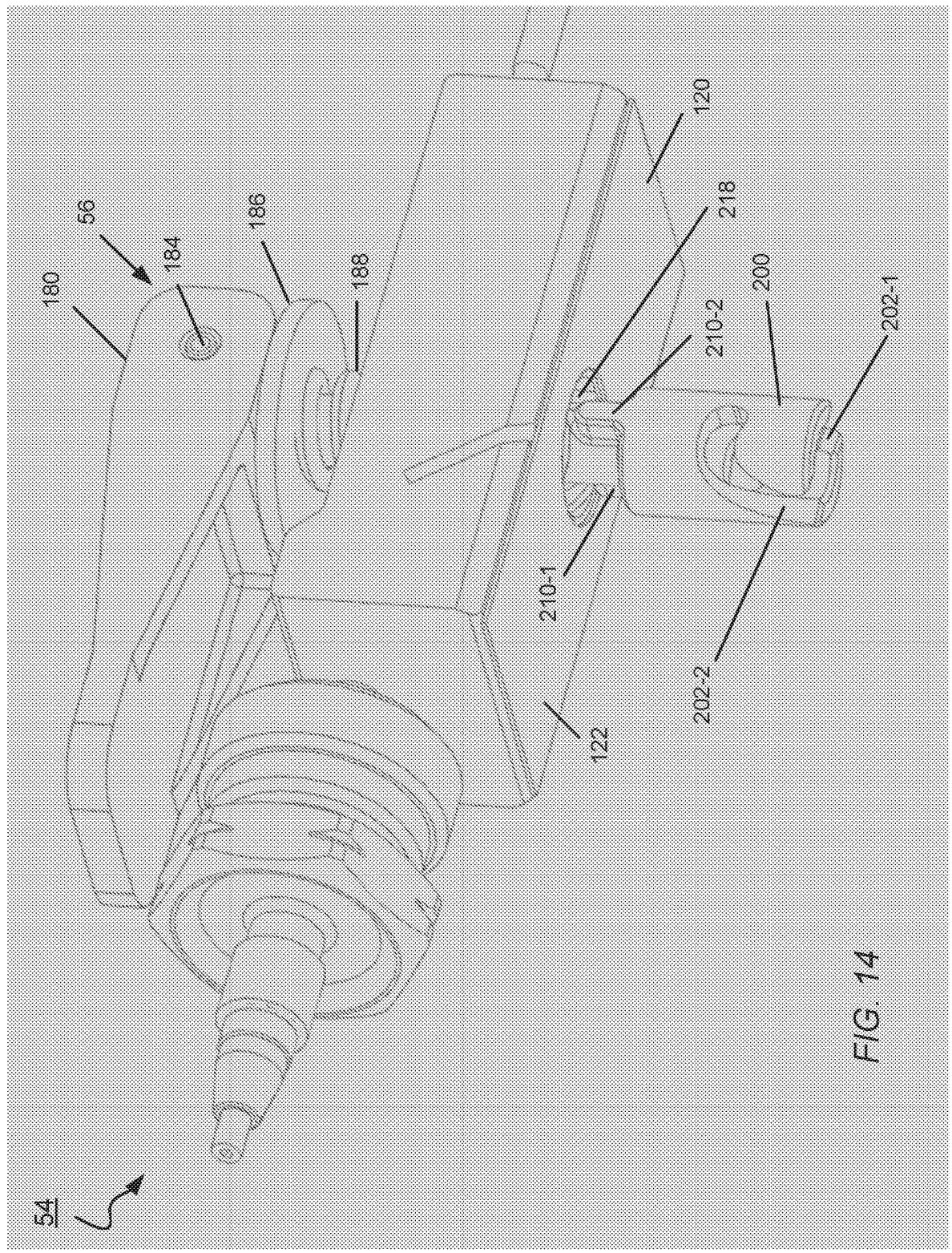
FIG. 14 is an elevated side view of the fluidic block with the retention mechanism of FIG. 12 extending therethrough.

FIG. 14 shows an elevated side view of the fluidic block 54 with the retention mechanism 56 of FIG. 12 extending therethrough. On this side of the fluidic block 54, the helical groove 202-2 and prong 210-2 of the plunger portion 200 are in the foreground, whereas the other helical groove 202-1 and prong 210-1 are in the background. In addition, this view shows the extent to which the plunger portion 200 extends beyond the bottom of the fluidic block 54 when the retention mechanism 56 is in the locked position. When the retention mechanism 56 is raised vertically and turned by 90 degrees, the prongs 210 of the plunger portion 200 are drawn along the inclined ramps 208 (FIG. 13) into the bore 218 of the fluidic block 54 by force of the spring 188.

Figure 15:
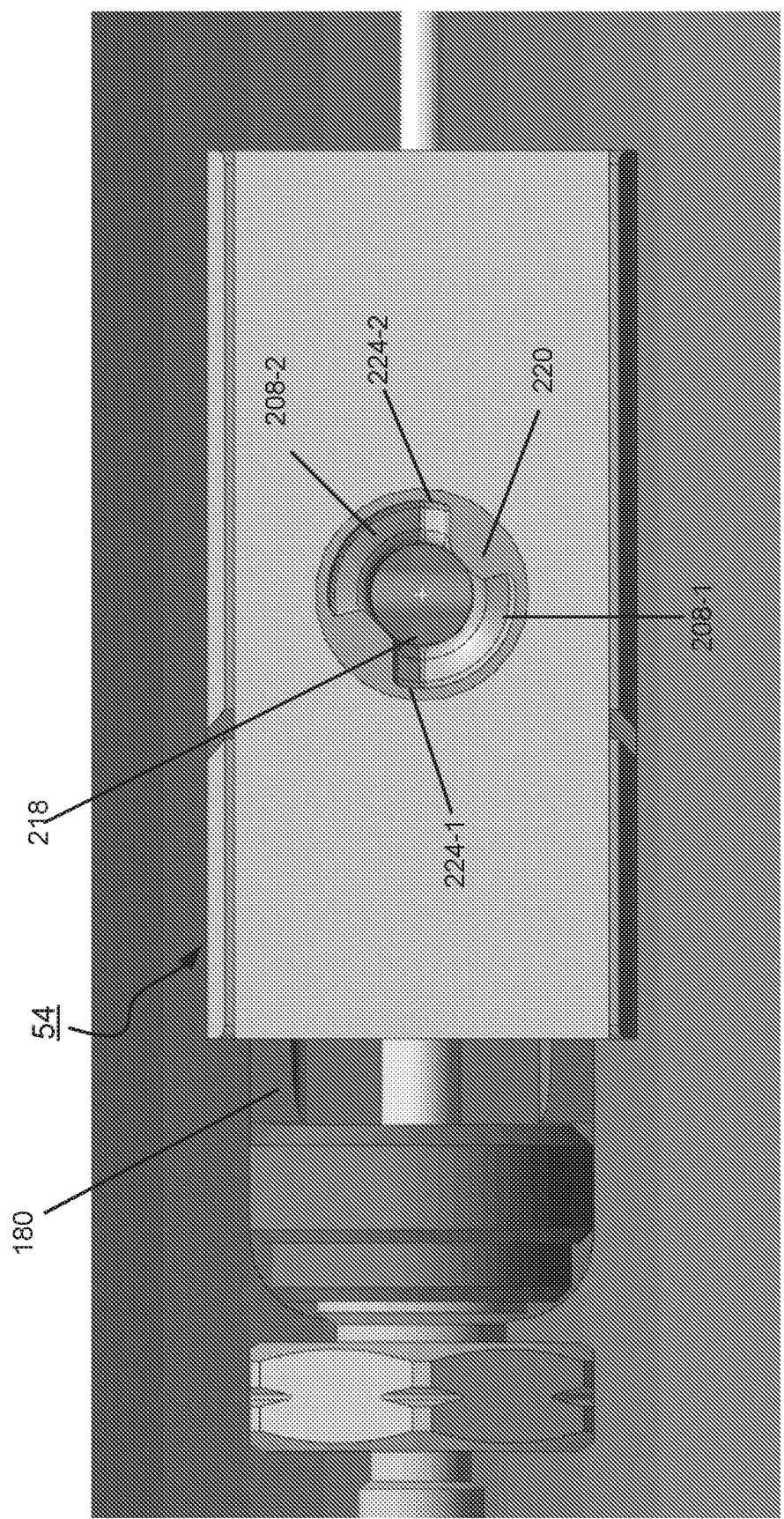
FIG. 15 is a bottom view of the fluidic block having arcuate ramps cast in the fluidic block.

FIG. 15 shows a bottom view of the fluidic block 54 having a circular region 220 surrounding the bore 218 of the fluidic block 54. On opposite sides of the ring 220 are the arcuate ramps 208-1 and 208-2. Each ramp 208-1, 208-2 has a depressed notch 224-1, 224-2, respectively (referred to previously as a depression). The notches 224-1, 224-2 (generally, 224) are directly opposite each other across the opening into the bore 218. Each depressed notch 224 receives the tip of a prong 210 of the plunger portion 200 when the retention mechanism 56 is in the locked position. Operating as seats for the prongs 210, these notches 224 provide a tactile sense that the fluidic block 54 and thermal base 52 have been properly secured to each other. With the prongs 210 so seated, the notches 224 provide a degree of resistance to incidental turning of the lever 180 when the retention mechanism 56 is locked (the helical shape of each groove 202 in the plunger portion 200 contributing to this resistance). In addition, each notch 224 abuts one raised end of the ramp 208 to limit the extent of the turning of the lever 180. On the other side of each notch 224, the ramp 208 gradually declines (into the plane of the figure).

While the invention has been shown and described with reference to specific preferred embodiments, it should be understood by those skilled in the art that various changes in form and detail may be made therein without departing from the spirit and scope of the invention as defined by the following claims. For example, the aforementioned embodiments describe two-piece active pre-heaters, whereas embodiments of one-piece active pre-heaters, wherein the fluidic block is inseparable from the thermal base, can also benefit from the temperature measurement accuracy achieved by thermally isolating the thermistor assembly from the thermal base and from the use of thermal breaks to guide heat flow in the fluidic block.

What is claimed is:

1. A fluidic block, comprising:
    a thermally conductive body having a first end and a second end opposite the first end, the thermally conductive body having a cutout portion formed therein between the first and second ends, the cutout portion partitioning the thermally conductive body into a first region, a second region, and a thin region between the first and second regions, the thin region having a cross sectional area that is less than a cross sectional area of the first region and a cross sectional area of the second region, the cutout portion producing a thermal break between the first and second regions, the thermal break operating to guide a heat flow between the first and second regions through the thin region, the thermally conductive body having a hole extending from a first side of the thermally conductive body through to an opposite, second side of the thermally conductive body;
    a thermally conductive tube extending through the first, second, and thin regions from the first end to the second end of the thermally conductive body, the thermally conductive tube being in thermal communication with the thermally conductive body; and
    a retention mechanism including:
        a lever portion movably abutting the first side of the thermally conductive body;
        a shaft coupled to the lever portion, the shaft extending through the hole in the thermally conductive body; and
        a plunger portion coupled to the shaft on the second side of the thermally conductive body,
    wherein the lever portion has a first position that extends the plunger portion from the hole and a second position that retracts the plunger portion towards the hole.

2. The fluidic block of claim 1, wherein the thermally conductive tube is cast within the thermally conductive body.

3. The fluidic block of claim 1, wherein the thermally conductive tube is diffusion bonded within the thermally conductive body.

4. The fluidic block of claim 1, wherein a section of the thermally conductive tube runs in a transverse direction across the thermally conductive body in the thin region of the thermally conductive body.

5. The fluidic block of claim 1, further comprising a column fitting coupled to one end of the thermally conductive tube.

6. The fluidic block of claim 1, wherein the first region is near the first end of the thermally conductive body and the second region is near the second end of the thermally conductive body, and the cutout portion angles away from the first end of the thermally conductive body towards the second end of the thermally conductive body.

7. The fluidic block of claim 1, wherein the plunger portion has a tapered end that widens to a shoulder and from the shoulder narrows to a neck where the plunger meets the shaft, and wherein the thermally conductive body has circumferential recess in the hole around the shaft, and further comprising:
    a spring disposed in the recess in the hole around the shaft to provide an opposing force to any force applied to the tapered end of the plunger portion.

8. The fluidic block of claim 1, wherein the plunger portion has one or more helical grooves adapted to receive a pin throughout a 90-degree turn of the lever portion.

9. The fluidic block of claim 1, wherein the retention mechanism further comprises a spring disposed around the shaft, the second side of the thermally conductive body has one or more exterior-facing ramps formed therein around the hole, and the plunger portion has one or more prongs facing the one or more ramps, the spring being adapted to urge each prong against one of the one or more ramps throughout a 90-degree turn of the lever portion.

10. The fluidic block of claim 9, wherein each ramp has a depressed notch for receiving a tip of one of the one or more prongs when the lever portion is turned into the first position.

11. The fluidic block of claim 1, wherein the thermally conductive body houses no electrical components.

12. A chromatography column pre-heating apparatus comprising:
    a heater assembly having a thermally conductive base and a heater in thermal communication with the thermally conductive base; and
    a fluidic block coupled to the heater assembly, the fluidic block comprising:
        a thermally conductive body having a first end and a second end opposite the first end, the thermally conductive body having a cutout portion formed therein between the first and second ends, the cutout portion partitioning the thermally conductive body into a first region, a second region, and a thin region between the first and second regions, the thin region having a cross sectional area that is less than a cross sectional area of the first region and a cross sectional area of the second region, the first region being in thermal communication with the thermally conductive base near the heater of the heater assembly, the cutout portion producing a thermal break between the first and second regions, the thermal break operating to guide conduction of heat produced by the heater from the first region to the second region through the thin region, the thermally conductive body has a hole extending from a first side of the thermally conductive body through to an opposite, second side of the thermally conductive body;
        a thermally conductive tube extending through the first, second, and thin regions from the first end to the second end of the thermally conductive body, the thermally conductive tube being in thermal communication with the thermally conductive body and heated by the heat produced by the heater; and a retention mechanism including:
: a lever portion movably abutting the first side of the thermally conductive body;
: a shaft coupled to the lever portion, the shaft extending through the hole in the thermally conductive body; and
: a plunger portion coupled to the shaft on the second side of the thermally conductive body,
: wherein the lever portion has a first position that extends the plunger portion from the hole and a second position that retracts the plunger portion towards the hole.

13. The chromatography column pre-heating apparatus of claim 12, wherein the thermally conductive tube within the fluidic block is cast within the thermally conductive body of the fluidic block.

14. The chromatography column pre-heating apparatus of claim 12, wherein the thermally conductive tube within the fluidic block is diffusion bonded within the thermally conductive body of the fluidic block.

15. The chromatography column pre-heating apparatus of claim 12, wherein a section of the thermally conductive tube runs in a transverse direction across the thermally conductive body in the thin region of the thermally conductive body.

16. The chromatography column pre-heating apparatus of claim 12, wherein the fluidic block further comprises a column fitting coupled to one end of the thermally conductive tube.

17. The chromatography column pre-heating apparatus of claim 12, wherein the first region is near the first end of the thermally conductive body and the second region is near the second end of the thermally conductive body, and the cutout portion angles away from the first end of the thermally conductive body towards the second end of the thermally conductive body.

18. The chromatography column pre-heating apparatus of claim 12, wherein the plunger portion has one or more helical grooves adapted to receive a pin throughout a 90-degree turn of the lever portion.

19. The chromatography column pre-heating apparatus of claim 12, wherein the retention mechanism further comprises a spring disposed around the shaft, the second side of the thermally conductive body has one or more exterior-facing ramps formed therein around the hole, and the plunger portion has one or more prongs facing the one or more ramps, the spring being adapted to urge each prong against one of the one or more ramps throughout a 90-degree turn of the lever portion.

20. The chromatography column pre-heating apparatus of claim 19, wherein each ramp has a depressed notch for receiving a tip of one of the one or more prongs when the lever portion is turned into the first position.

21. The chromatography column pre-heating apparatus of claim 12, wherein the plunger portion has a tapered end that widens to a shoulder and from the shoulder narrows to a neck where the plunger portion meets the shaft, and wherein the thermally conductive body has a circumferential recess in the hole around the shaft, and further comprising:
: a spring disposed in the recess in the hole around the shaft to provide an opposing force to any force applied to the tapered end of the plunger portion.

22. The chromatography column pre-heating apparatus of claim 12, wherein the body houses no electrical components.

23. A chromatography column module comprising:
: a chromatography column;
: a pre-heating apparatus coupled to the chromatography column, the pre-heating apparatus comprising:
:: a heater assembly having a thermally conductive base and a heater in thermal communication with the thermally conductive base; and
:: a fluidic block coupled to the heater assembly and to the chromatography column, the fluidic block comprising:
::: a thermally conductive body having a first end and a second end opposite the first end, the thermally conductive body having a cutout portion formed therein between the first and second ends, the cutout portion partitioning the thermally conductive body into a first region, a second region, and a thin region between the first and second regions, the thin region having a cross sectional area that is less than a cross sectional area of the first region and a cross sectional area of the second region, the first region being in thermal communication with the thermally conductive base near the heater of the heater assembly, the cutout portion producing a thermal break between the first and second regions, the thermal break operating to guide conduction of heat produced by the heater from the first region to the second region through the thin region; and
::: a thermally conductive tube coupled to the chromatography column, the thermally conductive tube extending through the first, second, and thin regions from the first end to the second end of the thermally conductive body, the thermally conductive tube being in thermal communication with the thermally conductive body and heated by the heat produced by the heater; and
: a cover for closing a compartment that houses the chromatography column and the pre-heating apparatus; and
: wherein the pre-heating apparatus includes a retention mechanism to couple the fluidic block to the heater assembly, the retention mechanism having a lever portion used to couple the fluidic block to and uncouple the fluidic block from the heater assembly, the lever portion preventing the cover from closing when in an uncoupled position, the unclosed cover preventing the heater of the heater assembly from operating.

24. The chromatography column module of claim 23, wherein a section of the thermally conductive tube runs in a transverse direction across the thermally conductive body in the thin region of the thermally conductive body.

25. A chromatography column pre-heating apparatus comprising:
: a fluidic block comprising:
:: a thermally conductive body having a first end and a second end opposite the first end, the thermally conductive body having a cutout portion formed therein between the first and second ends, the cutout portion partitioning the thermally conductive body into a first region, a second region, and a thin region between the first and second regions, the thin region having a cross sectional area that is less than a cross sectional area of the first region and a cross sectional area of the second region, the cutout portion producing a thermal break between the first and second regions, the thermal break operating to guide conduction of heat from the first region to the second region through the thin region; and
:: a thermally conductive tube extending through the first, second, and thin regions from the first end to the second end of the thermally conductive body, the thermally conductive tube being in thermal communication with the thermally conductive body; and a heater assembly coupled to the fluidic block, the heater assembly comprising:
- a thermally conductive base having a cavity and a chamber, the cavity being disposed opposite the first region of the fluidic block and the chamber being disposed opposite the second region of the fluidic block;
- a heater disposed within the cavity in thermal communication with the thermally conductive base, the first region of the thermally conductive body being in thermal communication with the thermally conductive base near the heater, the heater producing heat that propagates into the fluidic block; and
- a thermistor assembly disposed within the chamber of the thermally conductive base, the thermistor assembly having a temperature-sensing element substantially isolated thermally from the thermally conductive base, the thermistor assembly having a surface in thermal communication with the second region of the fluidic block to conduct heat from the second region of the fluidic block to the temperature-sensing element, the temperature-sensing element measuring a temperature of the second region of the fluidic block substantially uninfluenced by a temperature of the thermally conductive base because of the thermal isolation of the temperature-sensing element from the thermally conductive base.

* * * * *